(12) United States Patent
Patel et al.

(10) Patent No.: US 12,311,107 B2
(45) Date of Patent: May 27, 2025

(54) SEAL FOR A PATIENT INTERFACE, INTERFACE ASSEMBLIES AND ASPECTS THEREOF

(71) Applicant: Fisher & Paykel Healthcare Limited, Auckland (NZ)

(72) Inventors: Roheet Patel, Auckland (NZ); Peter David Alexander Bearne, Auckland (NZ); Michael John Henri Cox, Auckland (NZ); Fadi Karim Moh'd Mashal, Auckland (NZ); Kirstin Elizabeth Middelkoop, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 162 days.

(21) Appl. No.: 17/858,704

(22) Filed: Jul. 6, 2022

(65) Prior Publication Data
US 2023/0043746 A1 Feb. 9, 2023

Related U.S. Application Data

(63) Continuation of application No. 14/907,135, filed as application No. PCT/NZ2014/000158 on Aug. 5, 2014, now Pat. No. 11,419,999.
(Continued)

(51) Int. Cl.
*A61M 16/06* (2006.01)
(52) U.S. Cl.
CPC ........ *A61M 16/0616* (2014.02); *A61M 16/06* (2013.01); *A61M 16/0611* (2014.02);
(Continued)

(58) Field of Classification Search
CPC .............. A61M 16/0616; A61M 16/06; A61M 16/0605; A61M 16/0611; A61M 16/0666;
(Continued)

(56) References Cited

U.S. PATENT DOCUMENTS

| 235,643 A | 12/1880 | Nolen |
| 443,191 A | 12/1890 | Illing |

(Continued)

FOREIGN PATENT DOCUMENTS

| AU | 2004201337 A1 | 10/2005 |
| CN | 101378810 | 3/2009 |

(Continued)

OTHER PUBLICATIONS

U.S. Appl. No. 14/354,550, filed Apr. 25, 2017, Beane et al.
(Continued)

*Primary Examiner* — Elliot S Ruddie
(74) *Attorney, Agent, or Firm* — VIA LLP

(57) ABSTRACT

A mask assembly or interface with a mask assembly includes a mask seal and a mask shell that supports the mask seal. In some configurations, the mask assembly is configured to be fully positioned lower than a bridge of a nose of a face of a user and to provide an exposed bridge of the nose of the user. The mask seal includes one or more features that decouple movement of the nasal portion and the oral portion to allow relative movement therebetween at least about a longitudinal axis extending in the front to back direction of the mask seal. In some configurations, an interface assembly includes a movement limiting arrangement that limits movement of the upper portion of the mask seal.

18 Claims, 15 Drawing Sheets

Related U.S. Application Data

(60) Provisional application No. 62/013,417, filed on Jun. 17, 2014, provisional application No. 61/862,236, filed on Aug. 5, 2013.

(52) U.S. Cl.
CPC .... *A61M 16/0666* (2013.01); *A61M 16/0683* (2013.01); *A61M 2210/0618* (2013.01); *A61M 2210/0625* (2013.01)

(58) Field of Classification Search
CPC .......... A61M 16/0672; A61M 16/0683; A61M 2210/0618; A61M 2210/0625
USPC ...................................... 128/206.24, 206.28
See application file for complete search history.

(56) References Cited

U.S. PATENT DOCUMENTS

| | | |
|---|---|---|
| 804,272 A | 11/1905 | Schwarz |
| 1,229,050 A | 6/1917 | Donald |
| 1,445,010 A | 2/1923 | Feinberg |
| 2,228,218 A | 1/1941 | Schwartz |
| 2,317,608 A | 4/1943 | Heidbrink |
| 2,353,643 A | 7/1944 | Bulbulian |
| 2,403,046 A | 7/1946 | Bulbulian |
| 2,414,405 A | 1/1947 | Bierman et al. |
| 2,415,846 A | 2/1947 | Randall |
| 2,444,417 A | 7/1948 | Bierman |
| 2,540,567 A | 2/1951 | Bennett |
| 2,706,983 A | 4/1955 | Matheson et al. |
| 2,867,812 A | 1/1959 | Roth et al. |
| 2,875,757 A | 3/1959 | Galleher |
| 2,931,356 A | 4/1960 | Schwarz |
| 2,939,458 A | 6/1960 | Lundquist |
| 3,027,617 A | 4/1962 | Gray |
| 3,040,741 A | 6/1962 | Carolan |
| 3,092,105 A | 6/1963 | Gabb |
| 3,117,574 A | 1/1964 | Replogle |
| 3,170,463 A | 2/1965 | Duggan |
| 3,234,939 A | 2/1966 | Morton |
| 3,234,940 A | 2/1966 | Morton |
| 3,292,618 A | 12/1966 | Davis et al. |
| 3,295,529 A | 1/1967 | Corrigall et al. |
| 3,315,674 A | 4/1967 | Bloom et al. |
| 3,330,273 A | 7/1967 | Bennet |
| 3,330,274 A | 7/1967 | Bennet |
| 3,530,031 A | 9/1970 | Loew |
| 3,599,635 A | 8/1971 | Ansite |
| 3,680,555 A | 8/1972 | Warncke |
| 3,752,157 A | 8/1973 | Malmin |
| 4,263,908 A | 4/1981 | Mizerak |
| 4,384,577 A | 5/1983 | Huber et al. |
| 4,470,413 A | 9/1984 | Warncke |
| 4,603,692 A | 8/1986 | Montesi |
| 4,675,919 A | 6/1987 | Heine et al. |
| 4,764,989 A | 8/1988 | Bourgeois |
| 4,907,584 A | 3/1990 | McGinnis |
| 4,947,488 A | 8/1990 | Ashinoff |
| 4,960,121 A | 10/1990 | Nelson et al. |
| 5,005,571 A | 4/1991 | Dietz |
| 5,243,971 A | 9/1993 | Sullivan et al. |
| 5,323,516 A | 6/1994 | Hartmann |
| 5,441,046 A | 8/1995 | Starr et al. |
| 5,513,634 A | 5/1996 | Jackson |
| 5,517,986 A | 5/1996 | Starr et al. |
| 5,540,223 A | 7/1996 | Starr et al. |
| 5,560,354 A | 10/1996 | Berthon-Jones et al. |
| 5,570,684 A | 11/1996 | Behr |
| 5,570,689 A | 11/1996 | Starr et al. |
| 5,697,363 A | 12/1997 | Hart |
| 5,724,965 A | 3/1998 | Handke et al. |
| 5,832,918 A | 11/1998 | Pantino |
| 5,896,857 A | 4/1999 | Hely et al. |
| 5,934,276 A | 8/1999 | Fabro et al. |
| 6,016,804 A | 1/2000 | Gleason et al. |
| 6,119,694 A | 9/2000 | Correa et al. |
| 6,123,071 A | 9/2000 | Berthon-Jones et al. |
| 6,292,985 B1 | 9/2001 | Grunberger |
| 6,338,342 B1 | 1/2002 | Fecteau et al. |
| 6,341,382 B1 | 1/2002 | Ryvin et al. |
| 6,371,110 B1 | 4/2002 | Peterson et al. |
| 6,374,826 B1 | 4/2002 | Gunaratnam et al. |
| 6,422,238 B1 | 7/2002 | Lithgow |
| 6,467,483 B1 | 10/2002 | Kopacko et al. |
| 6,470,886 B1 | 10/2002 | Jestrabek-Hart |
| 6,491,034 B1 | 12/2002 | Gunaratnam et al. |
| 6,536,435 B1 | 3/2003 | Fecteau et al. |
| 6,584,975 B1 | 7/2003 | Taylor |
| 6,584,977 B1 | 7/2003 | Serowski |
| 6,598,271 B2 | 7/2003 | Nire |
| 6,598,272 B2 | 7/2003 | Nire |
| 6,606,767 B2 | 8/2003 | Wong |
| 6,644,316 B2 | 11/2003 | Bowman et al. |
| 6,647,597 B2 | 11/2003 | Reiter |
| 6,651,663 B2 | 11/2003 | Barnett et al. |
| 6,729,333 B2 | 5/2004 | Barnett et al. |
| 6,823,865 B2 | 11/2004 | Drew et al. |
| 6,823,869 B2 | 11/2004 | Raje et al. |
| 6,851,425 B2 | 2/2005 | Jaffre et al. |
| 6,851,428 B2 | 2/2005 | Dennis |
| 6,892,730 B2 | 5/2005 | Griffiths |
| 6,907,882 B2 | 6/2005 | Ging et al. |
| 6,990,691 B2 | 1/2006 | Klotz et al. |
| 7,000,614 B2 | 2/2006 | Lang et al. |
| 7,063,088 B1 | 6/2006 | Christopher |
| 7,152,602 B2 | 12/2006 | Bateman et al. |
| 7,210,481 B1 | 5/2007 | Lovell et al. |
| 7,260,440 B2 | 8/2007 | Selim et al. |
| 7,296,575 B1 | 11/2007 | Radney |
| 7,318,437 B2 | 1/2008 | Gunaratnam et al. |
| 7,353,826 B2 | 4/2008 | Sleeper et al. |
| 7,448,386 B2 | 11/2008 | Ho et al. |
| 7,509,958 B2 | 3/2009 | Amarisinghe et al. |
| 7,523,754 B2 | 4/2009 | Lithgow et al. |
| 7,556,043 B2 | 7/2009 | Ho et al. |
| 7,562,658 B2 | 7/2009 | Madaus et al. |
| 7,597,100 B2 | 10/2009 | Ging et al. |
| 7,658,189 B2 | 2/2010 | Davidson et al. |
| 7,708,017 B2 | 5/2010 | Davidson et al. |
| 7,721,737 B2 | 5/2010 | Radney |
| 7,762,254 B2 | 7/2010 | Ho |
| 7,793,987 B1 | 9/2010 | Busch et al. |
| 7,810,497 B2 | 10/2010 | Pittman et al. |
| 7,827,990 B1 | 11/2010 | Melidis et al. |
| 7,856,982 B2 | 12/2010 | Matula, Jr. et al. |
| 7,942,148 B2 | 5/2011 | Davidson et al. |
| 7,942,150 B2 | 5/2011 | Guney et al. |
| 7,958,893 B2 | 6/2011 | Lithgow et al. |
| 7,971,590 B2 | 7/2011 | Frater et al. |
| 7,975,694 B2 | 7/2011 | Ho |
| 7,992,560 B2 | 8/2011 | Burton et al. |
| 8,028,699 B2 | 10/2011 | Ho et al. |
| 8,042,538 B2 | 10/2011 | Ging et al. |
| 8,042,539 B2 | 10/2011 | Chandran et al. |
| 8,042,542 B2 | 10/2011 | Ging et al. |
| 8,122,886 B2 | 2/2012 | Kwok et al. |
| 8,127,764 B2 | 3/2012 | Ho et al. |
| 8,132,270 B2 | 3/2012 | Lang et al. |
| 8,136,523 B2 | 3/2012 | Rudolph |
| 8,136,524 B2 | 3/2012 | Ging et al. |
| 8,136,525 B2 | 3/2012 | Lubke et al. |
| 8,146,596 B2 | 4/2012 | Smith et al. |
| 8,146,597 B2 | 4/2012 | Kwok et al. |
| 8,196,583 B2 | 6/2012 | Radney |
| 8,205,615 B1 | 6/2012 | Ho |
| 8,251,066 B1 | 8/2012 | Ho |
| 8,254,637 B2 | 8/2012 | Abourizk et al. |
| 8,261,745 B2 | 9/2012 | Chandran et al. |
| 8,267,089 B2 | 9/2012 | Ho et al. |
| 8,291,906 B2 | 10/2012 | Kooij et al. |
| 8,297,285 B2 | 10/2012 | Henry et al. |
| 8,342,181 B2 | 1/2013 | Selvarajan et al. |
| 8,353,294 B2 | 1/2013 | Frater et al. |

(56) References Cited

U.S. PATENT DOCUMENTS

| | | |
|---|---|---|
| 8,397,728 B2 | 3/2013 | D'Souza et al. |
| 8,439,035 B2 | 5/2013 | Dantanarayana et al. |
| 8,490,623 B2 | 7/2013 | Berthon-Jones et al. |
| 8,490,624 B2 | 7/2013 | Ho et al. |
| 8,550,084 B2 | 10/2013 | Ng et al. |
| 8,573,212 B2 | 11/2013 | Lynch et al. |
| 8,596,271 B2 | 12/2013 | Matula, Jr. et al. |
| 8,616,211 B2 | 12/2013 | Davidson et al. |
| 8,622,057 B2 | 1/2014 | Ujhazy et al. |
| 8,636,007 B2 | 1/2014 | Rummery et al. |
| 8,646,449 B2 | 2/2014 | Browsher |
| 8,684,004 B2 | 4/2014 | Eifler |
| 8,701,667 B1 | 4/2014 | Ho et al. |
| 8,720,443 B2 | 5/2014 | Kooij et al. |
| 8,733,358 B2 | 5/2014 | Lithgow et al. |
| 8,757,157 B2 | 6/2014 | Price et al. |
| 8,770,190 B2 | 7/2014 | Doherty et al. |
| 8,800,563 B2 | 8/2014 | Doherty et al. |
| 8,807,134 B2 | 8/2014 | Ho et al. |
| 8,856,975 B2 | 10/2014 | Lang et al. |
| 8,857,435 B2 | 10/2014 | Matula, Jr. et al. |
| 8,869,797 B2 | 10/2014 | Davidson et al. |
| 8,875,709 B2 | 11/2014 | Davidson et al. |
| 8,910,626 B2 | 12/2014 | Matula, Jr. et al. |
| 8,931,484 B2 | 1/2015 | Melidis et al. |
| 8,944,061 B2 | 2/2015 | D'Souza et al. |
| 8,950,404 B2 | 2/2015 | Formica et al. |
| 8,967,146 B2 | 3/2015 | Veliss et al. |
| 8,978,653 B2 | 3/2015 | Frater et al. |
| 8,997,742 B2 | 4/2015 | Moore et al. |
| 9,010,330 B2 | 4/2015 | Barlow et al. |
| 9,010,331 B2 | 4/2015 | Lang et al. |
| 9,032,955 B2 | 5/2015 | Lubke et al. |
| 9,044,564 B2 | 6/2015 | Dravitzki et al. |
| 9,056,177 B2 | 6/2015 | Ho |
| 9,067,033 B2 | 6/2015 | Davidson et al. |
| 9,095,673 B2 | 8/2015 | Barlow et al. |
| 9,144,654 B2 | 9/2015 | Kwok |
| 9,149,593 B2 | 10/2015 | Dravitzki et al. |
| 9,149,594 B2 | 10/2015 | Kooij et al. |
| 9,155,857 B2 | 10/2015 | Lalonde |
| 9,174,018 B2 | 11/2015 | Ho et al. |
| 9,220,860 B2 | 12/2015 | Davidson et al. |
| 9,265,909 B2 | 2/2016 | Ho et al. |
| 9,295,805 B2 | 3/2016 | Worboys et al. |
| 9,381,316 B2 | 7/2016 | Ng et al. |
| 9,387,302 B2 | 7/2016 | Dravitzki et al. |
| 9,399,105 B2 | 7/2016 | Frater |
| 9,427,544 B2 | 8/2016 | Frater et al. |
| 9,480,809 B2 | 11/2016 | Guney et al. |
| 9,539,403 B2 | 1/2017 | Eves et al. |
| 9,717,870 B2 | 8/2017 | Kwok et al. |
| 9,737,678 B2 | 8/2017 | Formica et al. |
| 9,757,534 B2 | 9/2017 | Lang et al. |
| 9,764,107 B2 | 9/2017 | Grashow et al. |
| 9,889,267 B2 | 2/2018 | Wells et al. |
| 9,901,701 B2 | 2/2018 | Gunaratnam et al. |
| 9,962,511 B2 | 5/2018 | Ng et al. |
| 9,981,102 B2 | 5/2018 | Veliss et al. |
| 9,993,606 B2 | 6/2018 | Gibson et al. |
| 10,004,867 B2 | 6/2018 | Henry et al. |
| 10,130,785 B2 | 11/2018 | Dravitzki et al. |
| 10,188,819 B2 | 1/2019 | Chodkowski |
| 10,201,678 B2 | 2/2019 | Guney et al. |
| 10,220,171 B2 | 3/2019 | Olsen et al. |
| 10,265,490 B2 | 4/2019 | Barlow et al. |
| 10,265,492 B2 | 4/2019 | Amarasinghe et al. |
| 10,369,318 B2 | 8/2019 | Barlow et al. |
| 10,589,046 B2 | 3/2020 | Bearne et al. |
| 10,603,456 B2 | 3/2020 | Bearne et al. |
| 2002/0096178 A1 | 7/2002 | Ziaee |
| 2003/0127101 A1 | 7/2003 | Dennis |
| 2003/0172936 A1 | 9/2003 | Wilkie et al. |
| 2003/0196655 A1 | 10/2003 | Ging et al. |
| 2004/0107547 A1 | 6/2004 | Chung |
| 2004/0112377 A1 | 6/2004 | Amarasinghe et al. |
| 2004/0182396 A1* | 9/2004 | Dennis .................. A62B 18/02 128/205.25 |
| 2005/0028822 A1 | 2/2005 | Sleeper et al. |
| 2005/0056286 A1 | 3/2005 | Huddart et al. |
| 2005/0098183 A1 | 5/2005 | Nash et al. |
| 2005/0121030 A1 | 6/2005 | Bateman et al. |
| 2005/0199239 A1 | 9/2005 | Lang et al. |
| 2006/0042629 A1 | 3/2006 | Geist |
| 2006/0124131 A1 | 6/2006 | Chandran et al. |
| 2006/0174887 A1 | 8/2006 | Chandran et al. |
| 2006/0174892 A1 | 8/2006 | Leksutin et al. |
| 2006/0237017 A1 | 10/2006 | Davidson |
| 2006/0266365 A1 | 11/2006 | Stallard |
| 2006/0283461 A1 | 12/2006 | Lubke et al. |
| 2007/0006879 A1 | 1/2007 | Thornton |
| 2007/0125385 A1 | 6/2007 | Ho et al. |
| 2007/0144525 A1 | 6/2007 | Davidson et al. |
| 2007/0246043 A1 | 10/2007 | Kwok et al. |
| 2008/0041373 A1 | 2/2008 | Doshi et al. |
| 2008/0083412 A1 | 4/2008 | Henry et al. |
| 2008/0190432 A1 | 8/2008 | Blochlinger et al. |
| 2009/0038619 A1 | 2/2009 | Ho et al. |
| 2009/0044808 A1 | 2/2009 | Guney et al. |
| 2009/0107515 A1 | 4/2009 | Gavriely |
| 2009/0114229 A1 | 5/2009 | Frater et al. |
| 2009/0120442 A1 | 5/2009 | Ho |
| 2009/0139526 A1 | 6/2009 | Melidis |
| 2009/0173349 A1 | 7/2009 | Hernandez et al. |
| 2009/0277452 A1 | 11/2009 | Lubke et al. |
| 2010/0000543 A1 | 1/2010 | Berthon-Jones et al. |
| 2010/0000544 A1 | 1/2010 | Blaszczykiewicz |
| 2010/0006101 A1 | 1/2010 | McAuley |
| 2010/0083961 A1 | 4/2010 | McAuley et al. |
| 2010/0132717 A1 | 6/2010 | Davidson et al. |
| 2010/0192955 A1 | 8/2010 | Biener et al. |
| 2010/0218768 A1 | 9/2010 | Radney |
| 2010/0229872 A1 | 9/2010 | Ho |
| 2010/0313891 A1 | 12/2010 | Veliss et al. |
| 2011/0000492 A1 | 1/2011 | Veliss et al. |
| 2011/0067704 A1 | 3/2011 | Kooij et al. |
| 2011/0072553 A1 | 3/2011 | Ho |
| 2011/0146685 A1 | 6/2011 | Allan et al. |
| 2011/0162654 A1 | 7/2011 | Carroll et al. |
| 2011/0253143 A1 | 10/2011 | Ho et al. |
| 2011/0265796 A1 | 11/2011 | Amarasinghe et al. |
| 2011/0308526 A1 | 12/2011 | Ho et al. |
| 2011/0315143 A1 | 12/2011 | Frater |
| 2012/0067349 A1 | 3/2012 | Barlow et al. |
| 2012/0080035 A1 | 4/2012 | Guney et al. |
| 2012/0138061 A1 | 6/2012 | Dravitzki et al. |
| 2012/0138063 A1 | 6/2012 | Eves et al. |
| 2012/0152255 A1 | 6/2012 | Barlow et al. |
| 2012/0167892 A1 | 7/2012 | Matula, Jr. |
| 2012/0216819 A1 | 8/2012 | Raje et al. |
| 2012/0234326 A1 | 9/2012 | Mazzone et al. |
| 2012/0304999 A1 | 12/2012 | Swift et al. |
| 2012/0325219 A1 | 12/2012 | Smith |
| 2013/0000648 A1 | 1/2013 | Madaus et al. |
| 2013/0008446 A1 | 1/2013 | Carroll et al. |
| 2013/0037033 A1 | 2/2013 | Hitchcock et al. |
| 2013/0068230 A1 | 3/2013 | Jablonski |
| 2013/0133664 A1* | 5/2013 | Startare ............. A61M 16/0666 128/206.24 |
| 2013/0139822 A1 | 6/2013 | Gibson et al. |
| 2013/0152937 A1 | 6/2013 | Jablonski |
| 2013/0199537 A1 | 8/2013 | Formica |
| 2013/0213400 A1 | 8/2013 | Barlow et al. |
| 2013/0220327 A1 | 8/2013 | Barlow et al. |
| 2013/0263858 A1 | 10/2013 | Ho et al. |
| 2013/0306077 A1 | 11/2013 | Greenberg |
| 2013/0319422 A1 | 12/2013 | Ho et al. |
| 2013/0327336 A1 | 12/2013 | Burnham et al. |
| 2014/0026888 A1 | 1/2014 | Matula, Jr. et al. |
| 2014/0034057 A1 | 2/2014 | Todd et al. |
| 2014/0053844 A1 | 2/2014 | Rummery et al. |
| 2014/0069433 A1 | 3/2014 | Walker et al. |
| 2014/0094669 A1 | 4/2014 | Jaffe et al. |
| 2014/0158136 A1 | 6/2014 | Romagnoli et al. |

(56) References Cited

U.S. PATENT DOCUMENTS

| | | |
|---|---|---|
| 2014/0166018 A1 | 6/2014 | Dravitzki et al. |
| 2014/0166019 A1 | 6/2014 | Ho et al. |
| 2014/0174444 A1 | 6/2014 | Darkin et al. |
| 2014/0174446 A1 | 6/2014 | Prentice |
| 2014/0190486 A1 | 7/2014 | Dunn et al. |
| 2014/0202464 A1 | 7/2014 | Lithgow et al. |
| 2014/0209098 A1 | 7/2014 | Dunn et al. |
| 2014/0216462 A1 | 8/2014 | Law et al. |
| 2014/0224253 A1 | 8/2014 | Law et al. |
| 2014/0261412 A1 | 9/2014 | Guney et al. |
| 2014/0261432 A1 | 9/2014 | Eves et al. |
| 2014/0261434 A1 | 9/2014 | Ng et al. |
| 2014/0261435 A1 | 9/2014 | Rothermel |
| 2014/0261440 A1 | 9/2014 | Chodkowski |
| 2014/0283822 A1 | 9/2014 | Price et al. |
| 2014/0283826 A1 | 9/2014 | Murray et al. |
| 2014/0283831 A1 | 9/2014 | Foote et al. |
| 2014/0283841 A1 | 9/2014 | Chodkowski et al. |
| 2014/0283842 A1 | 9/2014 | Bearne et al. |
| 2014/0283843 A1 | 9/2014 | Eves et al. |
| 2014/0305439 A1 | 10/2014 | Chodkowski et al. |
| 2014/0311494 A1 | 10/2014 | Gibson et al. |
| 2014/0326243 A1 | 11/2014 | Znamenskiy et al. |
| 2014/0326246 A1 | 11/2014 | Chodkowski et al. |
| 2014/0352134 A1 | 12/2014 | Ho |
| 2014/0360503 A1 | 12/2014 | Franklin et al. |
| 2015/0007822 A1 | 1/2015 | Berthon-Jones et al. |
| 2015/0028519 A1 | 1/2015 | Lang et al. |
| 2015/0040911 A1 | 2/2015 | Davidson et al. |
| 2015/0047640 A1 | 2/2015 | McCaslin |
| 2015/0059759 A1 | 3/2015 | Frater et al. |
| 2015/0083124 A1 | 3/2015 | Chodkowski et al. |
| 2015/0105590 A1 | 4/2015 | Xiao |
| 2015/0128952 A1 | 5/2015 | Matula, Jr. et al. |
| 2015/0128953 A1 | 5/2015 | Formica et al. |
| 2015/0144139 A1 | 5/2015 | Lockhart |
| 2015/0174435 A1 | 6/2015 | Jones |
| 2015/0182719 A1* | 7/2015 | Grashow ............ A61M 16/0816 128/205.25 |
| 2015/0193650 A1 | 7/2015 | Ho et al. |
| 2015/0196726 A1 | 7/2015 | Skipper et al. |
| 2015/0246199 A1* | 9/2015 | Matula, Jr. ......... A61M 16/0622 128/206.24 |
| 2015/0290415 A1 | 10/2015 | Dunn |
| 2015/0352306 A1 | 12/2015 | Scheiner et al. |
| 2015/0352308 A1 | 12/2015 | Cullen et al. |
| 2016/0001029 A1 | 1/2016 | Bayer et al. |
| 2016/0022944 A1 | 1/2016 | Chodkowski et al. |
| 2016/0074613 A1 | 3/2016 | Davidson et al. |
| 2016/0082214 A1 | 3/2016 | Barlow et al. |
| 2016/0082216 A1 | 3/2016 | Lynch et al. |
| 2016/0175552 A1 | 6/2016 | Harrington |
| 2016/0184544 A1 | 6/2016 | Patel et al. |
| 2016/0271351 A1 | 9/2016 | Frater et al. |
| 2016/0296720 A1 | 10/2016 | Henry et al. |
| 2016/0367778 A1 | 12/2016 | Eves et al. |
| 2017/0000964 A1 | 1/2017 | Shafer |
| 2017/0021123 A1 | 1/2017 | Chang |
| 2017/0028153 A1 | 2/2017 | Judson et al. |
| 2017/0080174 A1 | 3/2017 | Eves et al. |
| 2017/0136200 A1 | 5/2017 | Matula, Jr. |
| 2017/0165444 A1 | 6/2017 | Rummery et al. |
| 2017/0182273 A1 | 6/2017 | Ho |
| 2017/0312467 A1 | 11/2017 | Davidson et al. |
| 2017/0326321 A1 | 11/2017 | Grashow et al. |
| 2017/0361048 A1 | 12/2017 | Moiler et al. |
| 2017/0368286 A1 | 12/2017 | Grashow et al. |
| 2018/0001044 A1 | 1/2018 | Stephens et al. |
| 2018/0071475 A1 | 3/2018 | Howard et al. |
| 2018/0099113 A1 | 4/2018 | Bell et al. |
| 2018/0104430 A1 | 4/2018 | Ng et al. |
| 2018/0140791 A1 | 5/2018 | Jones et al. |
| 2018/0169367 A1 | 6/2018 | Chodkowski et al. |
| 2018/0236198 A1 | 8/2018 | Veliss et al. |
| 2018/0250486 A1 | 9/2018 | Amarasinghe et al. |

FOREIGN PATENT DOCUMENTS

| | | |
|---|---|---|
| CN | 102698349 | 10/2012 |
| DE | 3719009 | 12/1988 |
| DE | 4004157 | 4/1991 |
| DE | 4307754 | 4/1994 |
| EP | 1099452 | 5/2001 |
| EP | 1152787 A1 | 11/2001 |
| EP | 1163923 | 12/2001 |
| EP | 1258266 A1 | 11/2002 |
| EP | 1912693 | 4/2008 |
| EP | 1938856 | 7/2008 |
| EP | 2060294 | 5/2009 |
| EP | 2130563 | 12/2009 |
| EP | 2303379 | 4/2011 |
| EP | 2417994 | 2/2012 |
| EP | 2437837 | 4/2012 |
| EP | 2452716 | 5/2012 |
| EP | 2470246 | 7/2012 |
| EP | 2474335 A1 | 7/2012 |
| EP | 2501425 | 9/2012 |
| EP | 2510968 | 10/2012 |
| EP | 2624902 | 8/2013 |
| EP | 2708258 | 3/2014 |
| EP | 2054114 B1 | 3/2015 |
| EP | 3164185 | 5/2017 |
| EP | 3254721 | 12/2017 |
| EP | 3305354 | 4/2018 |
| FR | 2390116 | 12/1978 |
| GB | 472897 | 9/1937 |
| GB | 521282 | 5/1940 |
| GB | 960115 | 6/1964 |
| GB | 1072741 | 6/1967 |
| GB | 2385533 | 8/2003 |
| GB | 2393126 | 3/2004 |
| JP | 2007-516750 | 6/2007 |
| JP | 2008-525123 | 7/2008 |
| JP | 2011-512967 | 4/2011 |
| JP | 2011-200744 | 10/2011 |
| JP | 2012-511371 | 5/2012 |
| JP | 2012-530561 | 12/2012 |
| NZ | 536545 | 12/2006 |
| NZ | 547748 | 7/2010 |
| WO | WO 94/02190 | 2/1994 |
| WO | WO 1998/034665 | 8/1998 |
| WO | WO 99/006116 | 2/1999 |
| WO | WO 00/38772 | 7/2000 |
| WO | WO 00/050122 | 8/2000 |
| WO | WO 2000/074758 | 12/2000 |
| WO | WO 2001/062326 | 8/2001 |
| WO | WO 02/07806 | 1/2002 |
| WO | WO 02/047749 | 6/2002 |
| WO | WO 03/013657 | 2/2003 |
| WO | WO 03/039637 | 5/2003 |
| WO | WO 2003/076020 | 9/2003 |
| WO | WO 03/090827 | 11/2003 |
| WO | WO 2004/041325 | 5/2004 |
| WO | WO 2004/071565 | 8/2004 |
| WO | WO 2004/073778 | 9/2004 |
| WO | WO 2005/018523 | 3/2005 |
| WO | WO 2005/032634 | 4/2005 |
| WO | WO 2005/063328 | 7/2005 |
| WO | WO 2005/076874 | 8/2005 |
| WO | WO 2005/086943 | 9/2005 |
| WO | WO 2005/118040 | 12/2005 |
| WO | WO 2005/118042 | 12/2005 |
| WO | WO 2006/130903 | 12/2006 |
| WO | WO 2007/012145 | 2/2007 |
| WO | WO 2007/143792 | 12/2007 |
| WO | WO 2008/023028 | 2/2008 |
| WO | WO 2008/030831 | 3/2008 |
| WO | WO 2008/063923 | 5/2008 |
| WO | WO 2009/026627 | 3/2009 |
| WO | WO 2009/059353 | 5/2009 |
| WO | WO 2009/065368 | 5/2009 |
| WO | WO 2009/143586 | 12/2009 |
| WO | WO 2010/066004 | 6/2010 |
| WO | WO 2010/067235 | 6/2010 |
| WO | WO 2010/073138 | 7/2010 |

(56) References Cited

FOREIGN PATENT DOCUMENTS

| WO | WO 2010/073142 | 7/2010 |
| WO | WO 2010/139014 | 12/2010 |
| WO | WO 2011/060479 | 5/2011 |
| WO | WO 2012/025843 | 3/2012 |
| WO | WO 2012/040791 | 4/2012 |
| WO | WO 2012/040792 A1 | 4/2012 |
| WO | WO 2012/045127 | 4/2012 |
| WO | WO 2012/055886 | 5/2012 |
| WO | WO 2013/056389 | 4/2013 |
| WO | WO 2013/066195 | 5/2013 |
| WO | WO 2013/128324 | 9/2013 |
| WO | WO 2013/142909 | 10/2013 |
| WO | WO 2013/175409 | 11/2013 |
| WO | WO 2013/186654 | 12/2013 |
| WO | WO 2014/020468 | 2/2014 |
| WO | WO 2014/021722 | 2/2014 |
| WO | WO 2014/025267 | 2/2014 |
| WO | WO 2014/045136 | 3/2014 |
| WO | WO 2014/045245 | 3/2014 |
| WO | WO 2014/062070 | 4/2014 |
| WO | WO 2014/077708 | 5/2014 |
| WO | WO 2014/110622 | 7/2014 |
| WO | WO 2014/141029 | 9/2014 |
| WO | WO 2014/165906 | 10/2014 |
| WO | WO 2014/175753 | 10/2014 |
| WO | WO 2014/177972 | 11/2014 |
| WO | WO 2014/181214 | 11/2014 |
| WO | WO 2014/183167 | 11/2014 |
| WO | WO 2015/006826 | 1/2015 |
| WO | WO 2015/020535 | 2/2015 |
| WO | WO 2015/068067 | 5/2015 |
| WO | WO 2015/070289 | 5/2015 |
| WO | WO 2015/092621 | 6/2015 |
| WO | WO 2015/161345 | 10/2015 |
| WO | WO 2015/193821 | 12/2015 |
| WO | WO 2016/000040 | 1/2016 |
| WO | WO 2016/041008 | 3/2016 |
| WO | WO 2016/041019 | 3/2016 |
| WO | WO 2016/075658 | 5/2016 |
| WO | WO 2017/049361 | 3/2017 |
| WO | WO 2017/103724 | 6/2017 |
| WO | WO 2017/120643 | 7/2017 |
| WO | WO 2017/124152 | 7/2017 |
| WO | WO 2017/185140 | 11/2017 |
| WO | WO 2018/064712 | 4/2018 |
| WO | WO 2018/177794 | 10/2018 |

OTHER PUBLICATIONS

U.S. Appl. No. 14/907,135, filed Jan. 22, 2016, Patel et al.
Amara View brochure, Respironics, 2015; product believed to have been available prior to Sep. 2015.
Australian Government, IP Australia, Examination Report No. 1 for Standard Patent Application No. 2014305231 dated Jan. 18, 2018 in 9 pgs.
Australian Government IP Australia, Examination Report No. 1 for Standard Patent Application No. 2013332513 dated Mar. 28, 2017 in 3 pgs.
Examination Report No. 1, Australian Government IP, Application No. 2015-275705, dated Feb. 25, 2019, in 4 pages.
Australian Examination Report No. 1 for Application No. 2020200999 dtd Jul. 13, 2020.
Australian Examination Report No. 1 for Application No. 2019261711 dated Jun. 12, 2020 in 4 pgs.
Brad T Miller, B. et al., A Head-and-Face Anthropometric Survey of U.S. Respirator Users, Final Report by Anthrotech, May 28, 2004 [retrieved from internet on Oct. 28, 2016].
Chinese Notification of the First Office Action, Application No. 201480044460.2, dated Feb. 27, 2017 in 15 pages.
Chinese Office Action for Application No. 201580024907.4 dated Apr. 28, 2018 in 8 pgs.
Official Action, Chinese Patent Office, Application No. 2016-571708, dated Feb. 28, 2019, in 3 pages.
European Patent Office Examination Report for Application No. 14835244.6 dated Feb. 14, 2019 in 8 pgs.
European Patent Office Examination Report, Application No. 13847504.1 dated Apr. 13, 2017 in 4 pgs.
European Patent Office , European Search Report for Application No. 14835244.6 dated Dec. 20, 2016, in 14 pages.
Extended European Search Report for PCT/IB2015/054560 dated Jan. 22, 2018 in 7 pgs.
Extended European Search Report for EP Appl. No. 16840943.1 dated Mar. 26, 2019 in 8 pages.
Extended European Search Report from EP 17857947.0 May 4, 2020 in 9 pgs.
Examination Report, Great Britain Application No. GB1602009.1, dated Aug. 1, 2019, in 4 pages.
Examination Report, Great Britain Application No. GB1602009.1, dated Dec. 19, 2019, in 4 pages.
Hsiao, H., Anthropometric Procedures for Protective Equipment Sizing and Design, Human Factors: The Journal of the Human Factors and Ergonomics Society, 55(1):6-35, Feb. 2013.
Japanese Patent Office, Official Action for ApplicationNo. 2015-537658 dated Aug. 23, 2017 in 5 pgs.
Lee, W. et al., Analysis of the Facial Measurements of Korean Air Force pilots for Oxygen Mask Design, Ergonomics, 56(9): 1451-64, 2013.
Los Alamos Scientific Laboratory Respirator and Research and Development Section, Selection of Respirator Test Panels Representative of U.S. Adult Facial Sizes, Dec. 1973 [retrieved from internet on Oct. 28, 2016].
International Search Report for PCT Application No. PCT/NZ2013/000189 dated Dec. 2, 2013.
International Search Report and Written Opinion for PCT/NZ2014/000158 mailed mailed Nov. 19, 2014 in 30 pgs.
International Search Report for PCT/IB2015/054560 dated Aug. 10, 2015 in 4 pgs.
International Search Report and Written Opinion for PCT/IB2016/055212 dated Oct. 31, 2016.
International Search Report for PCT Application No. PCT/IB2017/056136 dated Feb. 2, 2018 in 7 pages.
"International Standard ISO 17510-2 Sleep apnea breathing therapy—Part 2: Masks and application accessories".
Japanese Office Action for Application No. 2016-533273 dated Jun. 19, 2018 in 5 pgs.
Japanese Office Action for Application No. 2016-533273 dated May 24, 2019 in 4 pgs.
Written Opinion recevied from Intellectual Proeprty of Singapore for Applicatio NNo. 11201600431P dated Jun. 12, 2017.
Zhuang, Z. et al., Facial Anthropometric Differences among Gender, Ethnicity and Age Groups, The Annals of Occupational Hygiene, 54(4):391-402, Jun. 2010.

* cited by examiner

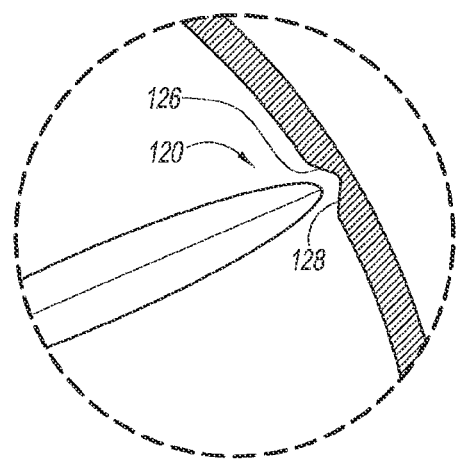
FIG. 5
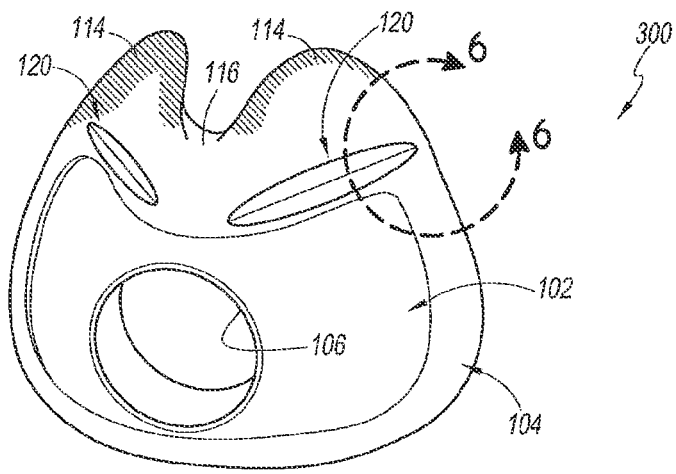
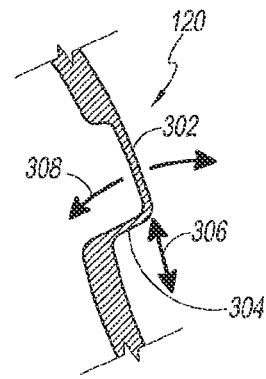
FIG. 6
FIG. 7A
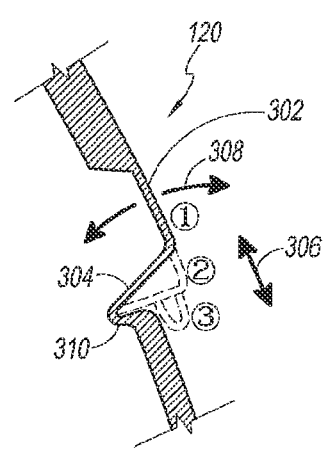
FIG. 7B

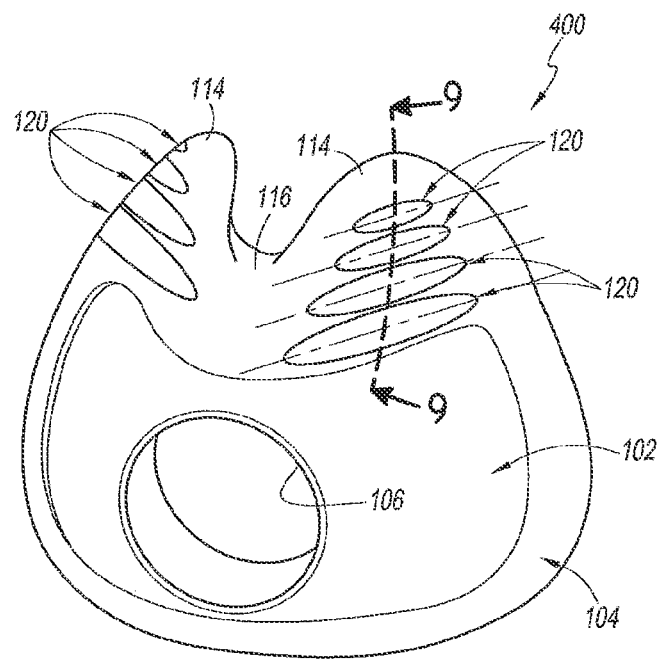
FIG. 8
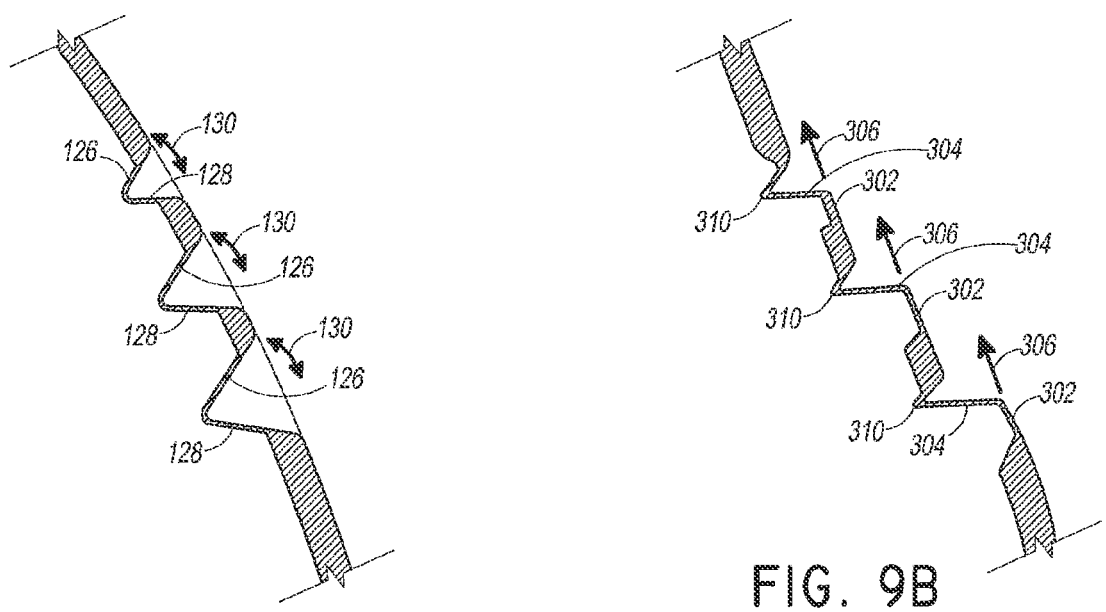
FIG. 9A
FIG. 9B

SEAL FOR A PATIENT INTERFACE, INTERFACE ASSEMBLIES AND ASPECTS THEREOF

INCORPORATION BY REFERENCE

The entireties of U.S. Provisional Application Nos. 61/862,236 and 62/013,417 are hereby incorporated by reference herein and made a part of the present disclosure.

BACKGROUND

Field

The disclosure generally relates to interface assemblies for providing a supply of pressurized gas to a recipient. In particular, the disclosure relates to interface assemblies and mask or seal assemblies for such interface assemblies.

Description of Related Art

Breathing gases can be delivered to users with a variety of different mask styles and can be delivered for a variety of different purposes. For example, users can be ventilated using non-invasive ventilation (NIV). In addition, continuous positive airway pressure (CPAP) or variable airway pressure can be delivered using masks to treat a medical disorder, such as obstructive sleep apnea (OSA), chronic obstructive pulmonary disease (COPD), or congestive heart failure (CHF).

These non-invasive ventilation and pressure support therapies generally involve the placement of a user interface device, which is typically a nasal or nasal/oral mask, on the face of a user. The flow of breathing gas can be delivered from the pressure/flow generating device to the airway of the user through the mask.

Typically, patient interface devices include a mask frame that supports a sealing member. The sealing member contacts the facial surfaces of the user, including regions surrounding the nose, including the nose and the nares. Because such masks are typically worn for an extended period of time, a variety of concerns must be taken into consideration. For example, in providing CPAP to treat OSA, the user normally wears the mask all night long while he or she sleeps. One concern in such a situation is that the mask should be as comfortable as possible. It is also important that the mask provide a sufficient seal against a user's face without significant discomfort.

SUMMARY

The systems, methods and devices described herein have innovative aspects, no single one of which is indispensable or solely responsible for their desirable attributes. The drawings are provided to illustrate example embodiments described herein and are not intended to limit the scope of the disclosure.

Some or all of the embodiments described herein address issues with stability that can be experienced with face masks. In this particular case, the embodiments are directed toward patient interfaces, such as face masks, which seal below the bridge of the user's nose and around the nares. But, the embodiments disclosed herein could also be adapted to other full face masks (e.g., those that partially cover and/or seal on the bridge of the user's nose). Most full face masks have a forehead rest, headgear mount or 'T' piece which extends upwardly from the remainder of the mask and rests on the forehead and adds significant stability compared to those full face masks without 'T' pieces. Instability can cause nose tip or septum pressure and/or seal leaks due to forces applied by the breathing tube of the breathing circuit that is attached to the mask or other patient interface. This force is often referred to as "hose pull" and can originate from the tube or from movement from the user.

Some of the embodiments illustrated herein have no T piece and seal below the bridge of the nose and around the nares and under the nose as well as around the user's mouth. The reduced foot print on the user's face compared to conventional full face masks can also have an adverse effect on stability. Sealing around and below the nose in this manner can present challenges due to the variation seen in facial geometries from user to user. In some circumstances, even small movements of the seal can induce loss of contact of the seal with the user, which can result in leaks.

Some or all of the embodiments disclosed herein address this issue by facilitating relative movement between an oral portion and a nasal portion of the mask or, as referred to herein, "decoupling" the oral portion from the nasal portion so one can move independent from the other in a rocking and/or pivoting motion. The headgear and hose/elbow attachment are generally attached to the oral portion of the seal (via a frame in some cases). Most external forces are transmitted to the seal via the headgear and hose pull. By decoupling the nasal portion from the oral in this manner the seal remains tolerant to external forces around the nasal portion, which generally is the area most susceptible to leak.

In some configurations, a mask assembly for an interface used in providing positive pressure respiratory therapy includes a mask seal and a mask shell that supports the mask seal. The mask assembly is configured to be fully positioned lower than a bridge of a nose of a face of a user and to provide an exposed bridge of the nose of the user. The mask shell includes a central portion and a pair of wings sweeping rearwardly of the central portion. An opening for a connector is formed in the mask shell in the central portion. The mask seal being connected to the mask shell. The mask seal having at least one oral opening on a lower portion and at least one nasal opening on an upper portion. The at least one oral opening being positioned opposite of the opening for the connector and the at least one nasal opening being positioned between the opening for the connector and the oral opening in a front to back direction. The mask seal further having one or more features that decouple movement of the nasal portion and the oral portion to allow relative movement therebetween at least about a longitudinal axis extending in the front to back direction of the mask seal.

In some such configurations, the nasal portion of the mask seal comprises at least one nasal element configured to engage a rare of the user.

In some such configurations, the at least one nasal element comprises a pair of nasal pillows that sealingly engage a respective one of the nares of the user.

In some such configurations, the nasal portion of the mask seal comprises a first paddle, a second paddle, and a nasal region having an upper support surface being positioned between the first paddle and the second paddle such that an upwardly-open valley is defined by the first paddle, the upper support surface and the second paddle, at least a portion of the at least one nasal opening being positioned on the upper support surface within the valley.

In some such configurations, the decoupling feature comprises an upper wall portion positioned directly above a lower wall portion and that are movable toward and away from one another. The upper wall portion and the lower wall portion can be generally linear to define a V-shape in cross-section. In some configurations, at least one of the upper wall portion and the lower wall portion has a curved shape in cross-section.

In some such configurations, the decoupling feature comprises a first wall portion and a second wall portion that are arranged at an angle relative to one another. The first wall portion and the second wall portion can cooperate to define an L-shape in cross-section. In some configurations, a curved wall portion between the second wall portion and a portion of the mask wall adjacent the decoupling feature. In some configurations, the first wall portion is shaped similarly to a front wall of the nasal portion of the mask assembly.

In some such configurations, the decoupling feature includes at least a first portion and a second portion positioned on opposite lateral sides of the mask assembly.

In some such configurations, a rigid connection portion is provided between the first portion and the second portion of the decoupling feature.

In some such configurations, a rigid strip portion is positioned above the first portion and the second portion of the decoupling feature.

In some such configurations, the decoupling feature further comprises additional portions on each lateral side arranged in a stacked configuration with the first portion and the second portion.

In some such configurations, the portions of each stacked configuration taper in size from the lowermost to the uppermost portions.

In some such configurations, the decoupling feature extends at least to a transition between a side surface and a user-facing surface of the mask assembly.

In some such configurations, the decoupling feature extends into the user-facing surface of the mask assembly.

In some such configurations, the decoupling feature defines an invert point at or near the transition.

In some such configurations, the decoupling feature tapers in height and or depth toward the invert point.

In some such configurations, the decoupling feature comprises a corrugated arrangement.

In some configurations, the mask assembly is combined with an interface component, the combination further comprising a movement limiting arrangement that limits movement of the upper portion of the mask seal.

In some such configurations, the movement limiting arrangement comprises one of a ratchet assembly, a cowling and a tether.

In some configurations, an interface for use in providing positive pressure respiratory therapy includes a mask assembly and a frame assembly. The mask assembly comprises a mask seal and a mask shell and is configured to be positioned on a face of a user covering the nose and/or mouth of the user. The mask shell comprises a central portion and a pair of wings sweeping rearwardly of the central portion. An opening for a connector is formed in the mask shell in the central portion. The mask seal is connected to the mask shell. The mask seal comprises a lower portion and an upper portion. At least one oral opening is positioned on the lower portion opposite of the opening for the connector. The mask assembly comprises one or more features that decouple movement of the nasal portion and the oral portion. The frame assembly is coupled to the mask assembly and configured for connection to a headgear. The interface further comprises a movement limiting arrangement that limits movement of the upper portion of the mask seal.

In some such configurations, the lower portion of the mask seal is connected to the mask shell.

In some such configurations, the lower portion and mask shell are relatively fixed when connected to the frame assembly. The upper portion is decoupled from the relatively fixed lower portion and mask shell.

In some such configurations, the relative movement of the decoupled upper portion includes forward and outward movement by way of inflation under gas pressure.

In some such configurations, the frame assembly includes features or covers to limit forward and outward relative movement of the nasal portion when the mask assembly is connected to the frame assembly.

In some such configurations, the movement limiting arrangement comprises one of a ratchet assembly, a cowling and a tether.

In some such configurations, the movement limiting arrangement is a ratchet assembly having a first ratchet portion coupled to the mask seal and a second ratchet portion coupled to the frame.

In some such configurations, the movement limiting arrangement is centrally located.

In some such configurations, the movement limiting arrangement comprises portions located on one or both lateral sides of the mask assembly.

In some such configurations, the movement limiting arrangement allows downward movement of the upper portion of the mask seal.

In some such configurations, the movement limiting arrangement limits, inhibits or prevents upward movement of the upper portion of the mask seal when the upper portion is expanded or when a gas pressure within the mask seal is at or above a threshold gas pressure.

In some such configurations, the movement limiting arrangement permits upward movement of the upper portion of the mask seal when the upper portion is not expanded or when the gas pressure within the mask seal is below a threshold gas pressure.

In some such configurations, the frame assembly is a common frame size connectable to mask assemblies of various sizes.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 5 is a front perspective view of another mask assembly having certain features, aspects and advantages of a preferred embodiment.

FIG. 6 is a sectional view of a decoupling feature of the mask assembly of FIG. 5.

FIGS. 7A and 7B are sectional views of alternative decoupling features.

FIG. 8 is a front perspective view of another mask assembly having certain features, aspects and advantages of a preferred embodiment.

FIGS. 9A and 9B are sectional views of alternative arrangements of a decoupling feature of the mask of FIG. 8.

DETAILED DESCRIPTION

FIGS. 1-32 illustrate several interfaces or mask assemblies (sometimes referred to simply as a "mask"), alone or in combination with other components of a related interface assembly or interface. The illustrated mask assemblies exhibit at least some decoupling properties between the nasal and oral portions. Although illustrated and described primarily in the context of a nasal-oral mask herein, the decoupling and/or other concepts disclosed herein could also be adapted to full face masks, including those with or without a forehead rest or T-piece, such as the arrangement disclosed in FIGS. 29 and 30.

Figure 1:
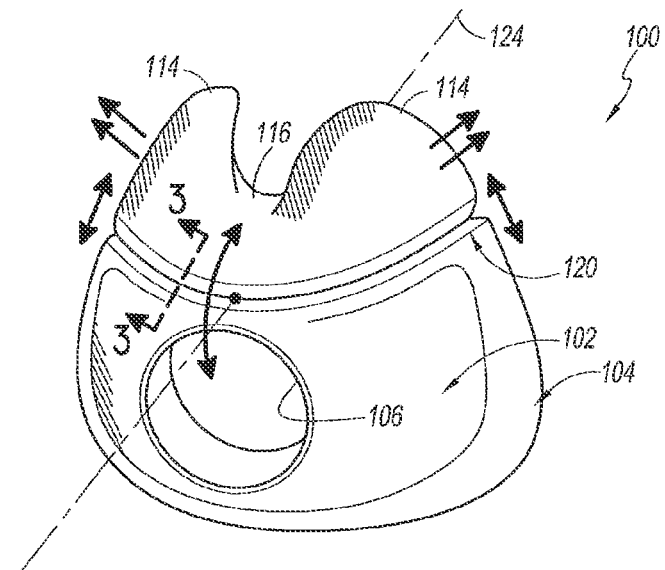
FIG. 1 is a front perspective view of a mask assembly having certain features, aspects and advantages of a preferred embodiment.
Figure 2:
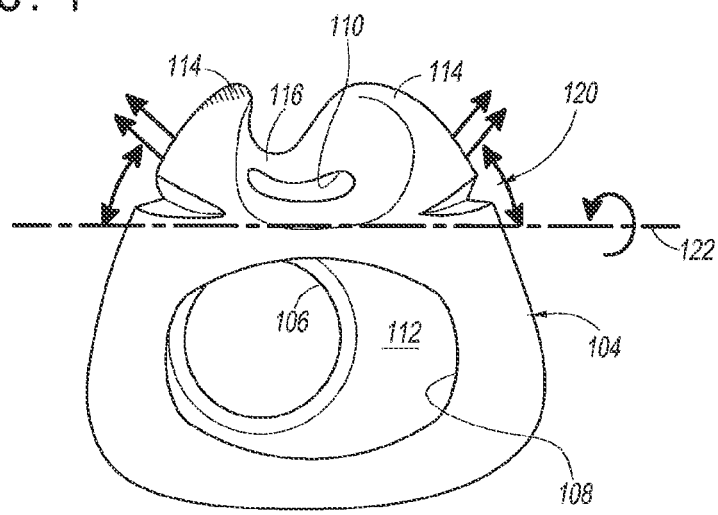
FIG. 2 is a rear perspective view of the mask assembly of FIG. 1.

FIGS. 1-3 illustrate a mask assembly 100 in the form of a combined nasal and oral mask, which can be referred to herein as a nasal-oral mask. The illustrated mask assembly 100 (and others disclosed herein unless indicated otherwise) is designed to seal under the nose of the user, along a portion of the face extending lateral to the nose, as well as around the mouth of the user. The mask assembly 100 advantageously does not require contact with the bridge of the nose of the user. In the illustrated configuration, the mask assembly 100 does not extend over the bridge of the nose of the user. More particularly, the illustrated mask assembly 100 does not contact the bridge of the nose of the user. Even more particularly, the illustrated mask assembly 100 does not contact a forward facing portion of the bridge of the nose of the user. In some configurations, the mask assembly 100 does not contact the face in a region vertically higher than a generally horizontal plane extending along the lower edges of the eyes of the user. The mask assembly 100 may or may not extend over the tip of the nose of the user. Thus, in some configurations, the mask assembly 100 covers the tip of the nose. In some configurations, the seal of the mask assembly covers the tip of the nose. In some configurations, the illustrated mask assembly 100 preferably does not enshroud the tip of the nose of the user. In some configurations or with some facial geometries, the tip of the nose of the user extends over the adjoining portion of the mask assembly 100.

The mask assembly 100 preferably is adapted to extend around and seal over the wing or alar of the nose, which flares out to form a rounded eminence around the nostril. The illustrated mask assembly 100 is adapted to seal around the surfaces that define the opening to the nostril, which may include a portion or entirety of the fleshy external end of the nasal septum, sometimes called the columella. In some configurations, the mask assembly 100 is adapted to extend upwardly to seal along at least a portion of the left and right dorsal side walls of the nose of the user. In some configurations, the mask assembly 100 is adapted to extend upwardly along at least a portion of the left and right dorsal side walls without extending upwardly to the region of the bridge of the nose of the user. In some configurations, a primary sealing surface of the mask assembly 100 contacts the underside of the nose of the user, possibly along with the upper lip and/or a transition region between the underside of the nose and the upper lip. A secondary sealing surface of the mask 100 can contact the side surfaces of the nose of the user, possibly along with the cheeks at a location near the nose. Such primary and secondary sealing surfaces may not make contact with the face of all users; however, such an arrangement can provide a suitable seal with a relatively large range of facial geometries. The mask assembly 100 preferably also seals around at least a portion of the user's mouth. The mask assembly 100 may or may not be adapted to seal between the mouth and nose of the user. Additional details of nasal-oral masks are described, for example, in connection with FIGS. 54-137 of Applicant's PCT Publication No. WO2014/062070, the entirely of which is hereby incorporated by reference herein and made a part of the present disclosure.

As illustrated, the mask assembly 100 comprises a mask support, such as a base, housing or shell 102, for example. A mask seal 104 can be attached to the mask shell 102 such that the mask shell 102 provides some amount of support for the mask seal 104. However, in other configurations, the mask seal 104 may not include a support and may be adapted for direct assembly to another component of the associated interface assembly. The mask assembly 100 can be engaged with, integrated with or otherwise supported by a frame that allows for connection to a head strap or headgear of any suitable arrangement. In some configurations, the head strap or headgear could be coupled directly to the mask assembly 100. A conduit connector, such as an elbow, can also be attached to the mask assembly 100 (mask shell 102 and/or seal 104), frame or otherwise supported relative to and adapted to communicate with an interior space of the mask assembly 100. The conduit connector facilitates connection to a gases conduit, such as a supply conduit or the like, for the supply of pressurized breathing gases. In some configurations, the conduit connector can include a vent, such as a bias flow vent, to allow venting of gases. In some configurations, a gases vent can be located elsewhere within the interface. Together, the frame and the headgear can support the mask assembly 100 in place on the user's face. Collectively, the mask assembly 100, frame and headgear can be referred to as an interface assembly. The mask assembly 100 or the mask assembly 100 in combination with a frame can be referred to as an interface.

The mask shell 102 provides a support structure of sorts for the mask assembly 100 in general and for the mask seal 104 more specifically. The mask shell 102 can be formed from any suitable material. In some configurations, the mask shell 102 is formed from a fairly rigid material. In some configurations, the mask shell 102 is formed from a plastic material, such as a polycarbonate material. In some configurations, the mask assembly 100 can comprise a mask seal that includes a mask seal clip that is separate from but attachable to a mask shell. In such a configuration, the mask seal clip would connect the mask seal to the mask shell. In such configurations, the mask seal and mask seal clip can be formed separately and secured together or the mask seal and the mask seal clip can be integrated into a single component. In some configurations, the mask seal can be overmolded onto the mask seal clip and, in some configurations, the mask seal can be overmolded directly onto the mask shell, which can comprise chemical or mechanical overmolding, for example.

In some configurations, the mask shell 102 comprises a substantial portion of a forward wall of the mask assembly 100. Such an arrangement provides an advantageous level of support to the mask seal 104. For example, the mask shell 102 comprises a substantial portion of an oral portion of the forward wall of the mask assembly 100. In some configurations, the mask shell 102 is generally limited to the oral portion of the mask assembly 100 and does not extend into the nasal portion of the mask assembly 100, at least to any significant extent. Such an arrangement can provide support to the mask seal 104, while advantageously permitting movement or deformation of the nasal portion of the mask seal 104. Thus, the lower or oral portion of the mask seal 104 can be relatively fixed when the mask assembly 100 is secured to a frame or other portion of an interface and the upper or nasal portion is decoupled from the relatively fixed lower or oral portion and mask shell 102. In the illustrated configuration, the mask shell 102 sweeps rearward from a central portion toward opposing side portions. The central portion contains an aperture 106 for receiving the conduit connector. The mask shell 102 can have a generally or substantially constant height throughout the central portion and opposing side portions. In other arrangements, the mask shell can vary in height. The height of the mask shell 102 can be substantially equal to a height of the oral portion of the mask seal 104. A width of the mask shell 102 can comprise a significant portion of the overall width of the oral portion of the mask assembly 100, such as at least about three-quarters of the overall width of the oral portion of the mask assembly 100. Such an arrangement of the mask shell 102 can provide reinforcement to the central and lateral portions of the mask seal 104. In some configurations, the mask shell 102 could be minimal, such as an annular support ring or perimeter frame, for example.

The mask seal 104 is designed to seal against the face of the user. The mask seal 104 preferably is formed of a soft material, such as silicone, for example but without limitation. As described above, the illustrated mask seal 104 comprises a nasal-oral mask seal and, therefore, comprises at least one oral opening 108 and at least one nasal opening 110. In some configurations, the mask seal 104 can comprise a combined oral-nasal opening. In some configurations, the mask seal 104 can comprise more than one nasal opening 124. In some configurations, the mask seal 104 can comprise nasal openings 124 defined within superstructures, such as pillows, prongs or the like. In some configurations, the nasal opening 124 can be defined by a nasal cushion or insert, which can be overmolded or otherwise secured to a base structure of the mask seal 104. An example of such an arrangement is disclosed in Applicant's PCT Publication No. WO 2014/062070.

The at least one oral opening 108 and the at least one nasal opening 110 preferably communicate with a single chamber 112 that is defined within the mask assembly 2100. The chamber 112 of the illustrated mask assembly 100 is at least partially defined by the mask shell 102 and the mask seal 104. The at least one oral opening 108 is substantially opposed to the aperture 106 that receives or communicates with the conduit connector. The at least one nasal opening 110 can be vertically above the at least one oral opening 108. The at least one nasal opening 110 can be positioned between the aperture 106 for the conduit connector and the at least one oral opening 108 in a fore-aft direction of the mask assembly 100. The at least one nasal opening 110 can have an axis that is inclined relative to vertical.

The mask seal 104 preferably comprises a pair of paddles 114 that extend upward above an upper surface 116 of a central portion of the mask seal 104. The upper surface 116 can define a line that lies along a central surface of the nasal surface of the mask seal 104 in a fore-aft direction. Such a line extends generally along the nasal septum in a direction away from the user's face. The paddles 114 are configured to extend upward alongside, and in some configurations above, the nares. The paddles 114 can contact the edges of the nares and/or sides of the nose. The paddles 114 or portions of the mask seal 104 between the paddles 114 may or may not cover the tip of the user's nose. As described herein, preferably the mask seal 104 does not contact the bridge of the user's nose. In some configurations, the paddles 114 each comprise an air pocket that is in direct fluid communication with the air path through the mask assembly 100 from the conduit connector to the at least one nasal opening 110 and the at least one oral opening 108. The paddles 114 can be configured to expand in volume in response to elevated pressure within the mask seal 2104 and/or flex inwardly to accommodate various facial and nasal geometries and assist in creating a sealed contact with the user's face. The height of the paddles 114 above the upper surface 116 can be selected to provide a desired balance between stability of the mask seal 104 on the user's face (e.g., vertical stability) and being able to accommodate a range of nasal geometries or reducing visual disruption by the paddles 114. In general, higher paddles 114 tend to provide additional vertical stability of the mask assembly 100, while lower paddles 114 tend to provide a better fit of a wider range of users and result in less visual disruption.

The illustrated mask seal 104 of the mask assembly 100 comprises a fairly complex range and configuration of thicknesses. The thicknesses are varied to take advantage of or provide different characteristics in different regions of the illustrated mask seal 104. For example, the thicknesses in the various regions can be selected to address a desired characteristic for that region and/or the mask seal 104 as a whole. Such characteristics can include, for example, allowing the mask seal 104 to conform to the facial geometry of the user to enhance sealing properties or comfort, supporting the shape of the mask seal without significant internal gas pressure to facilitate fitment and/or in response to internal gas pressure and/or external pressure (e.g., caused by headgear forces) or providing strength or durability.

In the illustrated configuration, the mask assembly 100 comprises a fold, hinge or bellows feature 120 (often collectively referred to as a "bellows feature" herein) configured to decouple the nasal and oral portions of the mask 100 (a "decoupling feature"). As used herein the nasal portion of the mask 100 refers to an upper portion of the mask 100 that contains the at least one nasal opening 110 and the oral portion of the mask 100 refers to a lower portion of the mask 100 that contains the at least one oral opening 108. In the illustrated arrangement, the bellows feature 120 is defined by the seal 104. In other configurations, the bellows feature 120 could be defined partially or entirely by the shell 102 or another portion or component of the mask 100. The bellows feature 120 preferably extends in a generally or substantially lateral direction on the mask 100 at or adjacent a transition between the nasal and oral portions of the mask 100. In some configurations, the bellows feature 120 extends along an upper edge of the shell 102.

In the illustrated configuration, the bellows feature 120 is provided on a forward-facing surface of the mask 100 and, preferably, wraps around the sides of the mask 100. However, preferably, the bellows feature 120 does not extend completely around a periphery of the mask 100, but terminates at or near approximately where the mask 100 contacts the face of the patient or user such that a portion or an entirety of the patient-contacting or user-contacting surface does not include the bellows feature 120. In some configurations, the bellows feature 120 permits the nasal portion to rotate about a lateral axis 122 located at or near the patient-contacting or user-contacting surface and between the oral portion and nasal portion of the mask 100. The lateral axis 122 can pass through or near the terminal ends of the bellows feature 120. In some configurations, the lateral axis 122 is positioned at a lower or rearward end of the upper surface 116 of the central portion of the seal 104 between the paddles 114. In some configurations, the bellows feature 120 permits the nasal portion to rotate about a longitudinal axis 124, which extends generally or substantially perpendicular to the lateral axis 122 in a fore-aft direction of the mask 100. The longitudinal axis 124 can pass through the lateral axis 122 and extend along a center of the mask 100. In some configurations, the nasal portion can rotate about either or both of the lateral axis 122 and the longitudinal axis 124 relative to the oral portion. Thus, movement of the nasal portion can have components of rotation about each of the lateral axis 122 and the longitudinal axis 124.

Figure 3A:
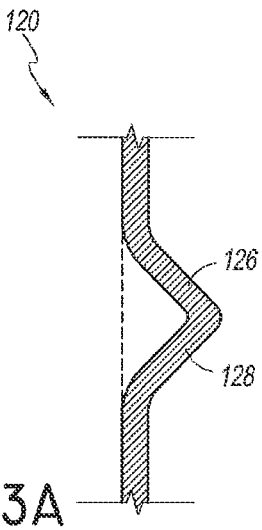
FIGS. 3A and 3B are sectional views of a decoupling feature of the mask assembly of FIG. 1 in two different positions.
Figure 3B:
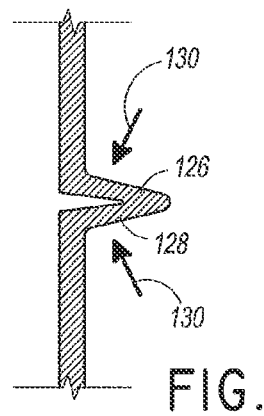

With reference to FIGS. 3A and 3B, in some configurations, the bellows feature 120 comprises an inwardly-extending fold having an upper wall portion 126 and a lower wall portion 128. In other configurations, the fold could extend outwardly. In the illustrated arrangement, the upper wall portion 126 is positioned directly above the lower wall portion 128 such that surfaces of the mask 100 above and below the bellows feature 120 are generally or substantially aligned with one another or such that the surfaces lie along a substantially continuous curve above and below the bellows feature 120, as illustrated by the dashed line in FIG. 3A. In other arrangements, the surfaces and/or walls of the mask 100 above and below the bellows feature 120 can be offset from one another. As illustrated in FIGS. 3A and 3B, the bellows feature 120 allows the fold to collapse such that the upper wall portion 126 and lower wall portion 128 move toward one another, thereby permitting relative movement between the nasal portion and the oral portion of the mask 100. Preferably, the bellows feature 120 allows collapse of the fold along any portion or an entirety of a length of the bellows feature 120 to permit a large variety of decoupling movement between the nasal portion and the oral portion of the mask 100. Such an arrangement can facilitate the mask 100 in maintaining a seal in both the nasal portion and the oral portion in response to a variety of forces acting on the mask 100, such as hose pull forces or headgear forces, for example. In some configurations, the bellows feature 120 permits the nasal portion of the seal to collapse to some extent relative to the oral portion when the headgear of the associated interface assembly is over-tightened.

In some configurations, the bellows feature 120 inhibits or substantially prevents translational movement between the upper wall portion 126 and the lower wall portion 128 and restrains the movement to folding, collapsing or rotational movement of the wall portions 126, 128 (as illustrated by arrows 130 in FIG. 3B) and/or nasal portion relative to the oral portion. Such an arrangement allows decoupled movement of the nasal and oral portions of the mask 100 while maintaining a desired fore-aft relationship therebetween. In some configurations, the bellows feature 120 is configured to limit or substantially avoid excessive separation of the upper wall portion 126 and 128 at least in response to internal gas pressure within the mask 100 to limit or avoid the nasal portion applying excessive pressure to the underside of the nose of the user or patient and causing discomfort. The permitted movement of the wall portions 126, 128 of the bellows feature 120 can be controlled by selection of materials, stiffness, wall thicknesses, wall shapes or any other suitable mechanism. In some configurations, the wall thickness of the upper wall portion 126 and/or lower wall portion 128 is substantially the same as or similar to adjacent wall thicknesses of the mask 100, such as portions immediately above and/or below the bellows feature 120. In other configurations, the wall thicknesses may vary between the upper wall portion 126 and/or lower wall portion 128 and adjacent wall thicknesses of the mask 100, including the portions immediately above and/or below the bellows feature 120. In addition, as described below, the bellows feature(s) can also be configured to permit translation, forward or outward movement of the nasal portion relative to the oral portion.

Figure 4:
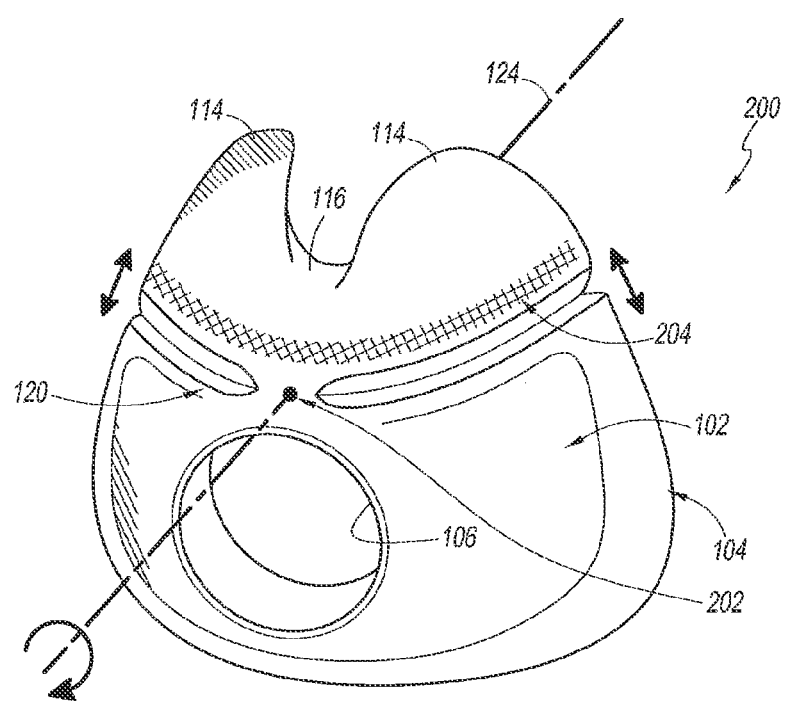
FIG. 4 is a front perspective view of another mask assembly having certain features, aspects and advantages of a preferred embodiment.

FIG. 4 illustrates a mask 200 that is substantially similar to the mask 100 of FIGS. 1-3. Accordingly, the same reference numbers are used to indicate the same, similar or corresponding components or features. In addition, the mask 200 is described in the context of differences relative to the mask 100. Therefore, components or features that are not explicitly described with respect to the mask 200 can be assumed to be the same as or substantially similar to the corresponding components or features of the mask 100, or can be of another suitable arrangement.

In the mask 200 of FIG. 3, the bellows feature 120 is interrupted at a substantially central, forward portion of the mask 200 by a relatively rigid connection portion 202 between the nasal and oral portions. The rigid connection portion 202 can be a portion of the mask 200 that omits the fold that creates the bellows feature 120. In other words, the rigid connection portion 202 can be similar to other portions of the mask 200 outside of the bellows feature 120 or similar to a mask that does not include a bellows feature 120. In some configurations, the rigid connection portion 202 could have increased stiffness relative to other portions of the mask 200, which can be provided by increased wall thickness, stiffening members or other suitable arrangements. The rigid connection portion 202 can limit, restrict, inhibit or substantially prevent movement of the nasal portion about a lateral axis relative to the oral portion of the mask 200, depending on the desired attributes or characteristics of the mask 200. Thus, decoupling motion can be at least somewhat restricted and, in some configurations, substantially restricted to relative movement about a longitudinal axis 124. Such an arrangement can limit or avoid collapse of the nasal portion relative to the oral portion in at least a central portion of the mask 200 under certain loading conditions, such as when the headgear of the associated interface assembly is tightened. Accordingly, forces can be transferred between the oral portion and the nasal portion of the mask 200 to, for example, ensure sealing contact of the nasal portion with the nose of the user or patient or providing tactile feedback to the user or patient indicating sealing contact with the nose in a configuration in which headgear forces are primarily applied to the oral portion. The rigid connection portion 202 can also inhibit or prevent excessive upward movement of the nasal portion relative to the oral portion of the mask 200, such as in response to relatively high internal pressure, to limit or avoid pressure on the underside of the nose of the user or patient. The folds of the bellows feature 120 can taper near the rigid connection portion 202 (as well as at opposite ends of the folds).

In some configurations, the mask 200 can include a rigid portion 204, such as a rigid strip, that extends in a lateral direction above the bellows feature 120. The rigid portion 204 can comprise a section or strip of increased material thickness and/or a separate structural member, for example and without limitation. Such an arrangement can facilitate pivoting of the nasal portion about the longitudinal axis 124 and improve the transfer of force from the nasal portion to the bellows feature 120 while maintaining desired performance of the nasal portion.

FIGS. 5-7 illustrate a mask 300 that is substantially similar to the masks 100 and 200. Accordingly, the same reference numbers are used to indicate the same, similar or corresponding components or features. In addition, the mask 300 is described in the context of differences relative to the masks 100 and 200. Therefore, components or features that are not explicitly described with respect to the mask 300 can be assumed to be the same as or substantially similar to the corresponding components or features of the other masks described herein, or can be of another suitable arrangement.

With reference to FIGS. 5 and 6, the mask 300 includes bellows features 120 that are provided on lateral portions of the mask 300 between the nasal and oral portions. Thus, two separate bellows features 120 can be provided. The bellows features 120 can mirror one another relative to a central, vertical plane of the mask 300. In the illustrated arrangement, a substantial gap is provided between the bellows features 120 relative to the arrangement of mask 200. Accordingly, decoupling movement can be restricted to a greater extent to movement about a longitudinal axis or substantially lateral movement of the nasal portion relative to the oral portion. In addition, the lateral ends of the bellows features 120 can terminate within a forward-facing surface of the mask 300. In other configurations, the bellows feature 120 can be a single feature that extends across the mask 300 and/or can extend closer to one another or into the rearward-facing surface of the mask 300.

The bellows features 120 can be somewhat oval in shape or tapered at one or both ends. As illustrated in FIG. 6, in some configurations, the bellows features 120 are defined by thinned sections or grooves within the wall of the mask 300. The grooves can be generally triangular in cross-sectional shape and define an upper surface 126 and a lower surface 128. The grooves can collapse to permit movement of the upper surface 126 and lower surface 128 toward one another in a manner similar to the upper wall portion 126 and lower wall portion 128 of the masks 100 and 200. However, the thinned regions or grooves are somewhat simpler in structure and can provide for easier manufacture. Although illustrated on an external surface of the mask 300, the bellows features 120 could alternatively (or additionally) be provided on an interior surface of the mask 300. Thus, internal and/or external grooves could be provided. In an arrangement having both internal and external grooves, such grooves could be aligned or staggered.

FIGS. 7A and 7B illustrate different variations of a wall structure configured to create the bellows feature 120. In the arrangement of FIG. 7A, the bellows feature 120 comprises an L-shaped (in cross-section) thinned wall portion, which offsets a wall portion of the mask 300 above the bellows feature 120 from a wall portion of the mask 300 below the bellows feature 120. The bellows feature 120 of FIG. 7A includes a first thinned wall portion 302 and a second thinned wall portion 304 that cooperate to define an L-shape in cross-section in a neutral position of the bellows feature 120 (e.g., absent a significant external force tending to cause relative movement between the nasal and oral portions of the mask 300). The first thinned wall portion 302 extends downwardly from the portion of the mask wall above the bellows feature 120. In the illustrated arrangement, the first thinned wall portion 302 extends in a continuous manner (e.g., a continuous curvature) from the portion of the mask wall above the bellows feature 120 and has a smaller wall thickness than at least the portion of the mask wall above the bellows feature 120. The second thinned wall portion 304 extends from a lower end of the first thinned wall portion 302 in a rearward direction and connects to a portion of the mask wall below the bellows feature 120. The second thinned wall portion 304 has a smaller wall thickness than at least a portion of the mask wall below the bellows feature 120. In the illustrated arrangement, the first thinned wall portion 302 and the second thinned wall portion 304 have the same or a similar wall thickness. In other arrangements, the first thinned wall portion 302 and the second thinned wall portion 304 can have different wall thicknesses.

The illustrated bellows feature 120 of FIG. 7A permits the nasal portion of the mask 300 to move downwardly relative to the oral portion as a result of downward movement of the second thinned wall portion 304 and/or collapse or deformation of the first thinned wall portion 302 as illustrated by the arrow 306. In some configurations, the bellows feature 120 can also permit forward movement of the nasal portion of the mask 300 relative to the oral portion as a result of buckling or other deformation of the first thinned wall portion 302 as illustrated by the arrows 308. In some configurations, such an arrangement can allow a greater amount of decoupled movement of the nasal portion compared to other arrangements of the bellows features 120 described herein, such as those of FIGS. 1-6, for example.

The illustrated bellows feature 120 of FIG. 7B is similar to the arrangement of FIG. 7A. The bellows feature 120 of FIG. 7B includes a first thinned wall portion 302 and a second thinned wall portion 304. However, wherein the second thinned wall portion 304 of FIG. 7A is attached at a forward edge of the portion of the mask wall below the bellows feature 120, the second thinned wall portion 304 of FIG. 7B is attached at a rearward edge of the portion of the mask wall below the bellows feature 120. In particular, the second thinned wall portion 304 is connected to the portion of the mask wall below the bellows feature 120 by a curved wall portion 310. In the illustrated arrangement, the curved wall portion 310 defines a relatively sharp curve that is positioned rearward of the portion of the mask wall below the bellows feature 120. However, in other arrangements, the curved wall portion 310 could be a more gradual curve and/or could be positioned above or in front of the portion of the mask wall below the bellows feature 120. The second thinned wall portion 304 could also be connected to the portion of the mask wall below the bellows feature 120 without the curved wall portion 310. In the illustrated arrangement of FIG. 7B, the second thinned wall portion 304 is angled downward from the first wall portion 302 such that the L-shaped bellows feature 120 defines an obtuse angle.

The bellows feature 120 of FIG. 7B allows for similar decoupled motion as the bellows feature 120 of FIG. 7A. However, the bellows feature 120 of FIG. 7B can allow for greater vertical movement of the nasal portion relative to the arrangement of FIG. 7A at least because the second thinned wall portion 304 can rotate as a result of collapse or deflection of the curved wall portion 310, as illustrated by the intermediate dashed line position (position 2). In addition, the second thinned wall portion 304 can collapse or deform in a manner similar to the arrangement of FIG. 7A, as illustrated in the lower dashed line position (position 3).

FIGS. 8 and 9 illustrate a mask 400 that is substantially similar to the masks 100, 200 and 300. Accordingly, the same reference numbers are used to indicate the same, similar or corresponding components or features. In addition, the mask 400 is described in the context of differences relative to the masks 100, 200 and 300. Therefore, components or features that are not explicitly described with respect to the mask 400 can be assumed to be the same as or substantially similar to the corresponding components or features of the other masks described herein, or can be of another suitable arrangement.

The mask 400 of FIG. 8 includes several bellows features 120 arranged in a vertical orientation or stack along each side of the nasal portion of the mask 400. The lowermost of the bellows features 120 can be sized, shaped and/or located in a manner substantially similar to the bellows feature 120 of FIG. 5. One or more additional bellows features 120 can be positioned above the lowermost bellows feature 120 extending toward or into the paddles 114. In the illustrated arrangement, a total of four bellows features 120 are provided on each lateral side of the mask 400; however, the numbers can vary in other arrangements, such as two, three, five or more bellows features 120. The bellows features 120 can be substantially similar in construction relative to one another, as illustrated, or could vary in construction, such as selected among any of the arrangements described herein. In some configurations, the bellows features 120 taper or reduce in dimensions (e.g., length, height, depth) moving from the bottom to the top.

FIG. 9A illustrates a cross-section of one suitable arrangement of the stacked bellows features 120 of FIG. 8. For example, each of the bellows features 120 can comprise inwardly-directed folds connecting portions of the front wall of the mask 400. The front wall of the mask 400 can have a substantially constant curvature and/or increase in thickness from top to bottom in a gradual manner ignoring the interruptions of the bellows features 120. Each bellows feature 120 can allow collapsed or folding of the upper wall portion 126 relative to the lower wall portion 128, as described in connection with FIGS. 3A and 3B. Collectively, the stacked bellows features 120 can permit a greater amount of decoupled movement or greater control or tuning of movement in various portions or at various locations (e.g., heights) of the nasal portion.

FIG. 9B illustrates an arrangement similar to FIG. 9A; however, each bellows feature 120 of FIG. 9B is substantially similar to an inverted arrangement of FIG. 7B in which a curved wall portion 310 connects a second thinned wall portion 304 to a first portion (e.g., upper portion) of the mask front wall and a first thinned wall portion 302 connects the second thinned wall portion 304 to a second portion (e.g., lower portion) of the mask front wall. Alternatively, the bellows features 120 could be arranged similar to FIG. 7B with the curved wall portion 310 located at the bottom of the bellows feature 120 or arranged similar to FIG. 7A without a curved wall portion 310. The front wall portion of the mask 400 can be stepped or offset and/or vary in thickness between the stacked bellows features 120.

Figure 10:
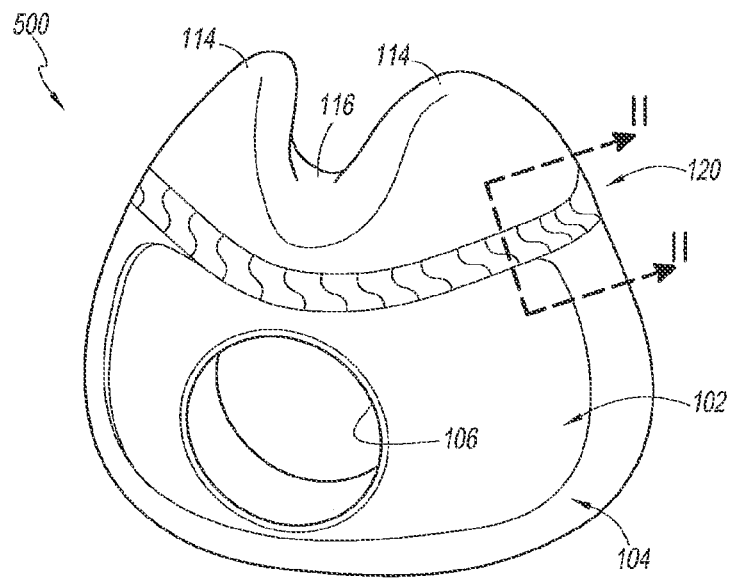
FIG. 10 is a front perspective view of another mask assembly having certain features, aspects and advantages of a preferred embodiment.
Figure 11:
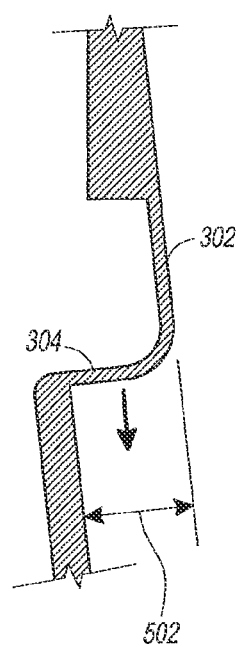
FIG. 11 is a sectional view of a decoupling feature of the mask assembly of FIG. 10.

FIGS. 10 and 11 illustrate a mask 500 that is substantially similar to the masks 100, 200, 300 and 400. Accordingly, the same reference numbers are used to indicate the same, similar or corresponding components or features. In addition, the mask 500 is described in the context of differences relative to the masks 100, 200, 300 and 400. Therefore, components or features that are not explicitly described with respect to the mask 500 can be assumed to be the same as or substantially similar to the corresponding components or features of the other masks described herein, or can be of another suitable arrangement.

The mask 500 of FIGS. 10 and 11 includes one or more bellows features 120 that fades out, becomes smaller or exhibits an increased resistance to folding toward the sides or back of the mask 500 relative to a forward, central portion of the one or more bellows features 120. The mask 500 can include a single bellows feature 120 extending across at least a substantial portion or entirety of a width of the front wall of the mask 500. In other configurations, the bellows feature 120 can be interrupted or split into multiple bellows features 120, such as the arrangements of FIG. 4 or 5, for example. Multiple bellows features 120 could be provided on each lateral side of the mask 500, if desired. In some configurations, the bellows feature(s) 120 extend toward or into a rear surface of the mask 500.

FIG. 11 illustrates an exemplary wall structure for the bellows feature(s) 120 of the mask 500. In the illustrated arrangement, the bellows feature 120 is the same as or similar to the arrangement of FIG. 7A and includes a first thinned wall portion 302 and a second thinned wall portion 304, which form an L-shape in cross-section and create an offset having an offset distance 502 between a wall portion of the mask 500 above the bellows feature 120 and a wall portion of the mask 500 below the bellows feature 120. In the mask 500, the offset distance 502 can vary along a length of the bellows feature 120 to create regions of varying resistance to decoupled movement. For example, the offset distance 502 could be reduced in the lateral ends of the bellows feature(s) 120 relative to side portions or more central portions. In addition on in the alternative, the offset distance 502 could be reduced in central portions of the bellows feature(s) 120 relative to more side portions and/or rearward portions. Thus, the offset distance 502 can be selected in various regions to tune the decoupling movement permitted in those regions. Other suitable arrangements for tuning the decoupled movement of the bellows feature(s) 120 can also be used, such as changes in wall thickness or stiffening members, for example. Other suitable wall profiles, such as any of those disclosed herein, could also be used and varied in one or more dimensions (e.g., offset, wall thickness) to allow the resistance to decoupling movement to be tuned or selected along a length of the bellows feature(s) 120.

Figure 12:
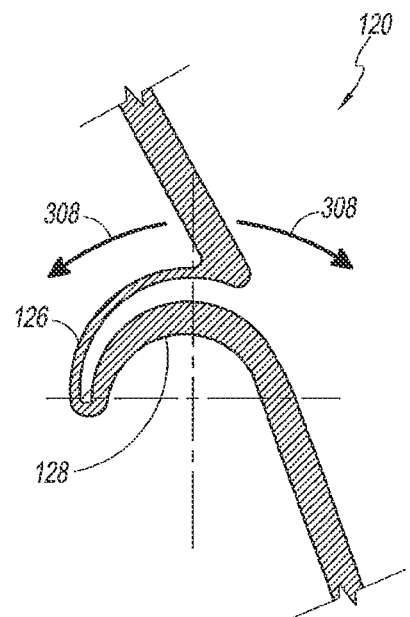
FIG. 12 is a sectional view of an alternative arrangement for a decoupling feature.
Figure 13:
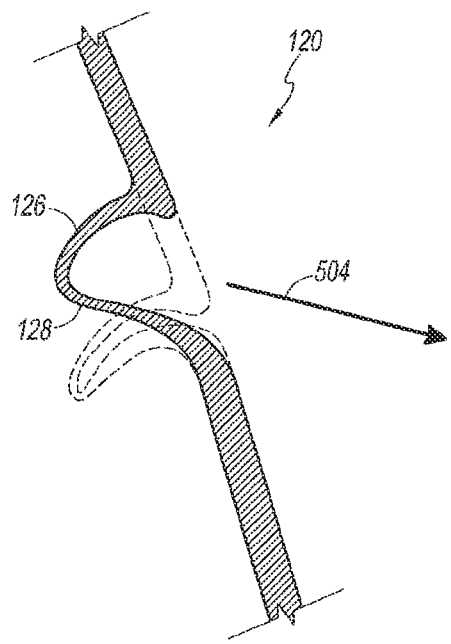
FIG. 13 is a section view of another alternative arrangement for a decoupling feature.

FIGS. 12 and 13 illustrate wall structures or arrangements that can be used to create a bellows feature 120, such as any of those described herein, for example. Each bellows feature 120 of FIGS. 12 and 13 includes an upper wall portion 126 and a lower wall portion 128 that can collapse, translate or otherwise move toward or relative to one another to allow decoupling movement of the nasal portion of the associated mask relative to the oral portion of the associated mask. In the arrangements of FIGS. 12 and 13, at least one of the upper wall portion 126 and the lower wall portion 128 are curved in cross-sectional shape. In the arrangement of FIG. 12, both the upper and lower wall portions 126, 128 are curved. In some configurations, the upper and lower wall portions 126, 128 are located relatively close to one another in a neutral position of the bellows feature 120 such that the decoupled movement substantially or primarily results from rolling or translational movement between the upper and lower wall portions 126, 128, as illustrated by the arrows 308. In the arrangement of FIG. 13, the upper wall portion 126 has greater curvature than the lower wall portion 128, which can be slightly curved or generally straight, for example. The arrangement of FIG. 13 can provide decoupled movement substantially or primarily as a result of collapse of the upper and lower wall portions 126, 128 toward one another, as illustrated by the position shown in dashed line. The wall structure of FIG. 13 can have advantages with respect to convenience of manufacturing relative to the wall structure of FIG. 12, such as improved ease of molding tool removal, for example. An exemplary tool pull direction 504 is illustrated by the arrow in FIG. 13.

Figure 14:
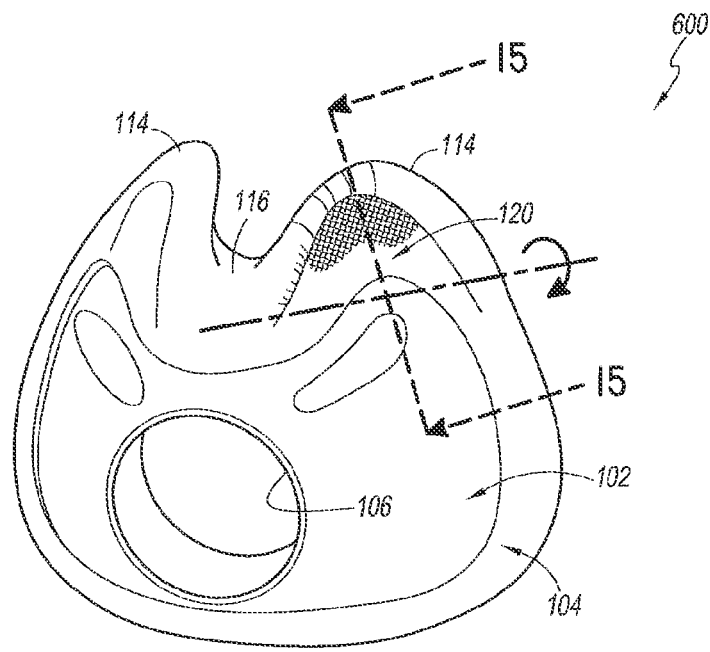
FIG. 14 is a front perspective view of another mask assembly having certain features, aspects and advantages of a preferred embodiment.
Figure 15:
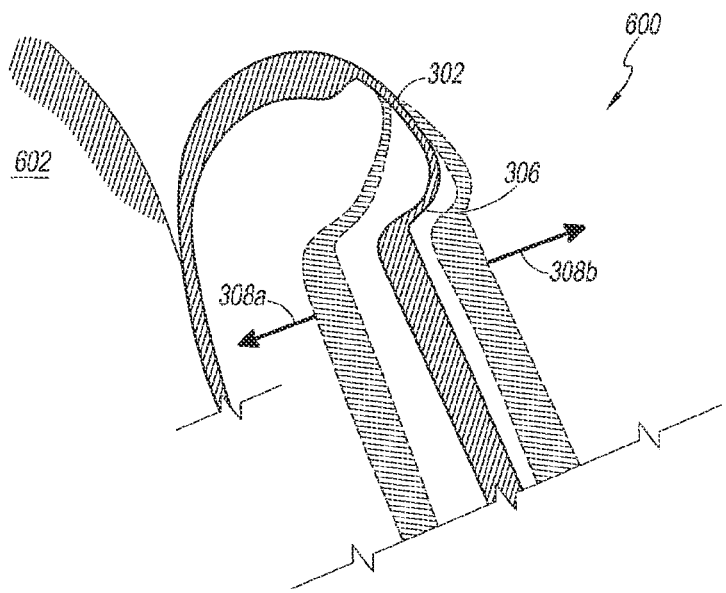
FIG. 15 is a sectional view of a decoupling feature of the mask assembly of FIG. 14.

FIGS. 14 and 15 illustrate a mask 600 that is substantially similar to the masks 100, 200, 300, 400 and 500. Accordingly, the same reference numbers are used to indicate the same, similar or corresponding components or features. In addition, the mask 600 is described in the context of differences relative to the masks 100, 200, 300, 400 and 500. Therefore, components or features that are not explicitly described with respect to the mask 600 can be assumed to be the same as or substantially similar to the corresponding components or features of the other masks described herein, or can be of another suitable arrangement.

The mask 600 of FIG. 14 includes a bellows feature 120 located on each side of the nasal portion, such as within each paddle 114. The bellows features 120 allow for or facilitate decoupled movement of the nasal portion relative to the oral portion. FIG. 15 illustrates a cross-section of the bellows feature 120, which includes a thinned wall section having, in the illustrated arrangement, a first thinned wall portion 302 and a second thinned wall portion 306 similar to the arrangement of FIG. 7A. However, in the illustrated arrangement, each of the bellows features 120 is shaped similar to and/or occupies a substantial entirety of a front wall of the paddles 114. In some configurations, one or both of the thinned wall portions 302, 306 can be curved and can follow a curvature of the mask 600, such as a curvature of the upper edge of the paddle 114. FIG. 15 illustrates movement of the wall of the mask 600 from a neutral position (intermediate position as a result of external forces, such as pressure on the nasal portion from the nose of the user or patient (which can result in the inward position toward the user's face 602 indicated by arrow 308*a*) or internal pressure from supplied breathing gases (which can result in the outward position away from the user's face 602 indicated by arrow 308*b*).

Figure 16:
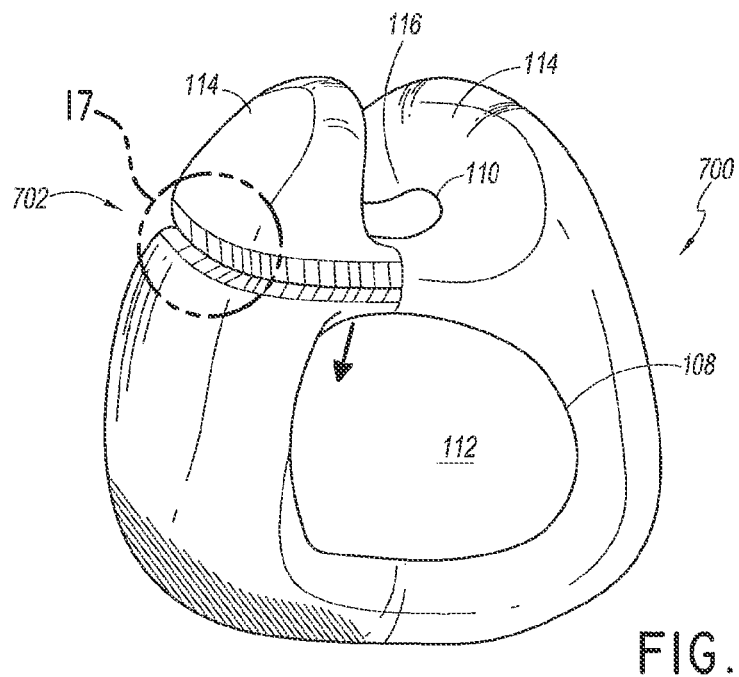
FIG. 16 is a rear perspective view of another mask assembly having certain features, aspects and advantages of a preferred embodiment.
Figure 17:
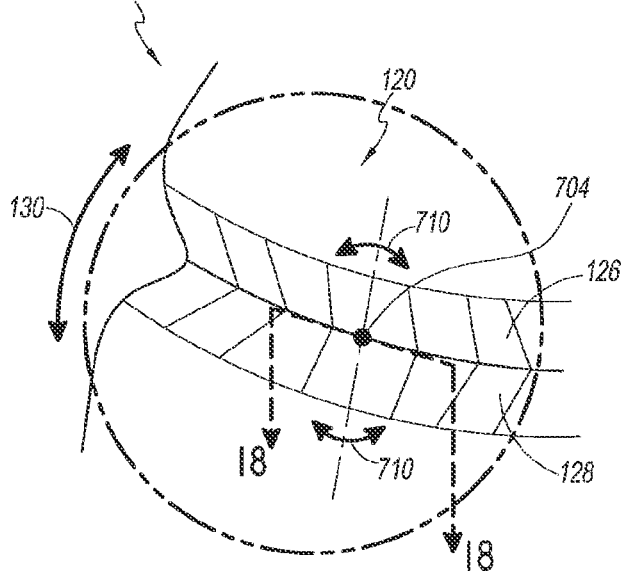
FIG. 17 is an enlarged view of a transition between a side surface and a rear or user-facing surface of the mask assembly of FIG. 16 illustrating a decoupling feature.
Figure 18:
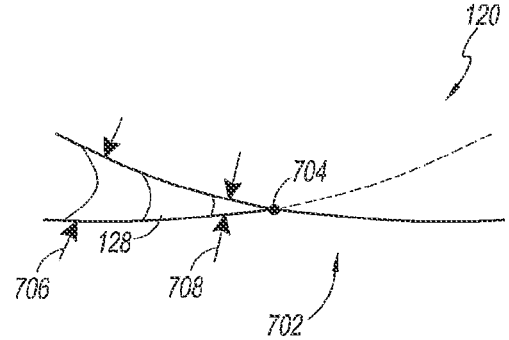
FIG. 18 is a sectional view of the mask assembly of FIGS. 16 and 17 taken along the line 18-18 of FIG. 17.

FIGS. 16-18 illustrate a mask 700 that is substantially similar to the masks 100, 200, 300, 400, 500 and 600. Accordingly, the same reference numbers are used to indicate the same, similar or corresponding components or features. In addition, the mask 700 is described in the context of differences relative to the masks 100, 200, 300, 400, 500 and 600. Therefore, components or features that are not explicitly described with respect to the mask 700 can be assumed to be the same as or substantially similar to the corresponding components or features of the other masks described herein, or can be of another suitable arrangement.

The mask 700 comprises a bellows feature 120 in the form of an elongate fold extending in a lateral direction across the mask 700 between the nasal portion and the oral portion in a manner similar to the bellows feature 120 of the mask 100. The bellows feature 120 can extend across a portion or an entirety of a front wall of the mask 700. In the illustrated arrangement, the bellows feature 120 extends toward or into the rear wall of the mask 700. FIGS. 16 and 17 illustrate a section of the bellows feature 120 near a transition 702 between a side surface and the user-facing or user-contacting surface. The bellows feature 120 can comprise a V-shaped fold including an upper wall portion 126 and a lower wall portion 128, similar to the arrangement illustrated in FIG. 3. The V-shaped fold can become shallower toward an invert point 704, which can be located at or near the transition 702 between the side surface and the patient-facing or patient-contacting surface. Thus, a first depth 706 of the V-shaped fold can be greater at a point further from the invert point 704 than a second depth 708 at a point closer to the invert point 704. After the invert point 704, the direction of the V-shaped fold can invert. For example, the V-shaped fold can change from inwardly-extending (e.g., forward of the invert point 704) to outwardly-extending (e.g., rearward of the invert point 704), as illustrated in FIG. 18. Such an arrangement can retain a desirable length of the transition 702 (or height of the mask 700) while permitting folding or a rolling pivotal motion (as indicated by the arrows 710) on one or both sides of the invert point 704.

Figure 19:
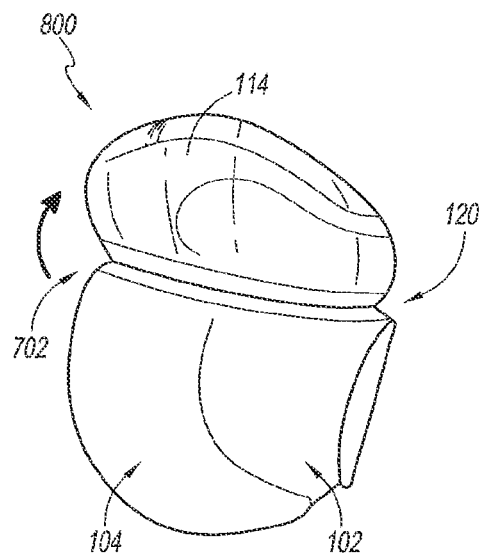
FIG. 19 is a side view of another mask assembly having certain features, aspects and advantages of a preferred embodiment.
Figure 20:
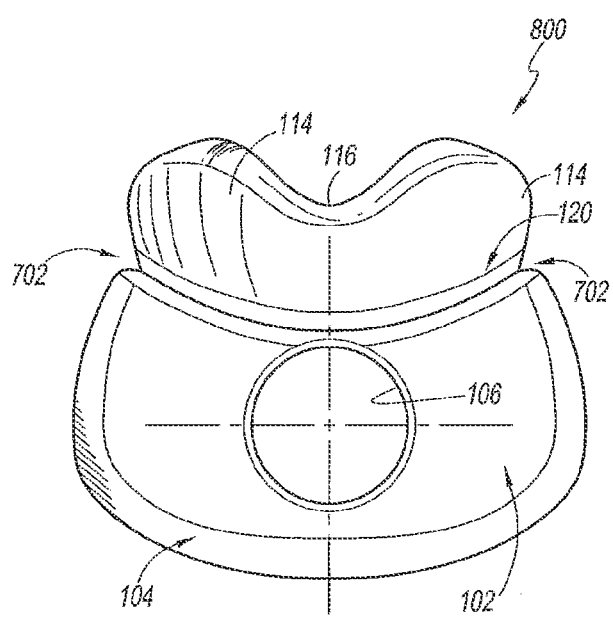
FIG. 20 is a front view of the mask assembly of FIG. 19.
Figure 21:
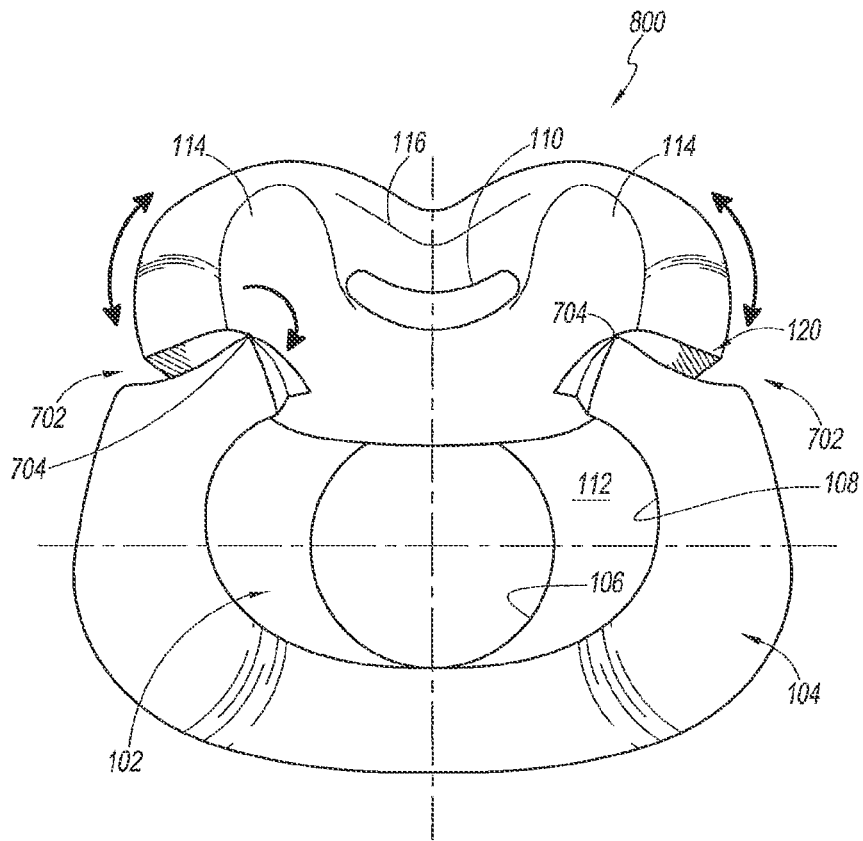
FIG. 21 is a rear view of the mask assembly of FIG. 19.

FIGS. 19-21 illustrate a mask 800 that is substantially similar to the masks 100, 200, 300, 400, 500, 600 and 700. Accordingly, the same reference numbers are used to indicate the same, similar or corresponding components or features. In addition, the mask 800 is described in the context of differences relative to the masks 100, 200, 300, 400, 500, 600 and 700. Therefore, components or features that are not explicitly described with respect to the mask 800 can be assumed to be the same as or substantially similar to the corresponding components or features of the other masks described herein, or can be of another suitable arrangement.

The mask 800 is similar to the mask 700 at least in that the bellows feature 120 tapers (in height and/or depth) to a pivot or invert point 704 at or near a transition 702 between a side surface and the patient-facing or patient-contacting surface. Compared to the mask 700, preferably, the pivot or invert point 704 can be located further rearward, closer together and more rearwardly-facing in the mask 800. In addition, the fold defining the bellows feature 120 extends downwardly inwardly of the pivot or invert points 704 between the nasal portion and the oral portion. In some configurations, the bellows feature 120 can extend to the at least one oral opening 108.

Figure 22:
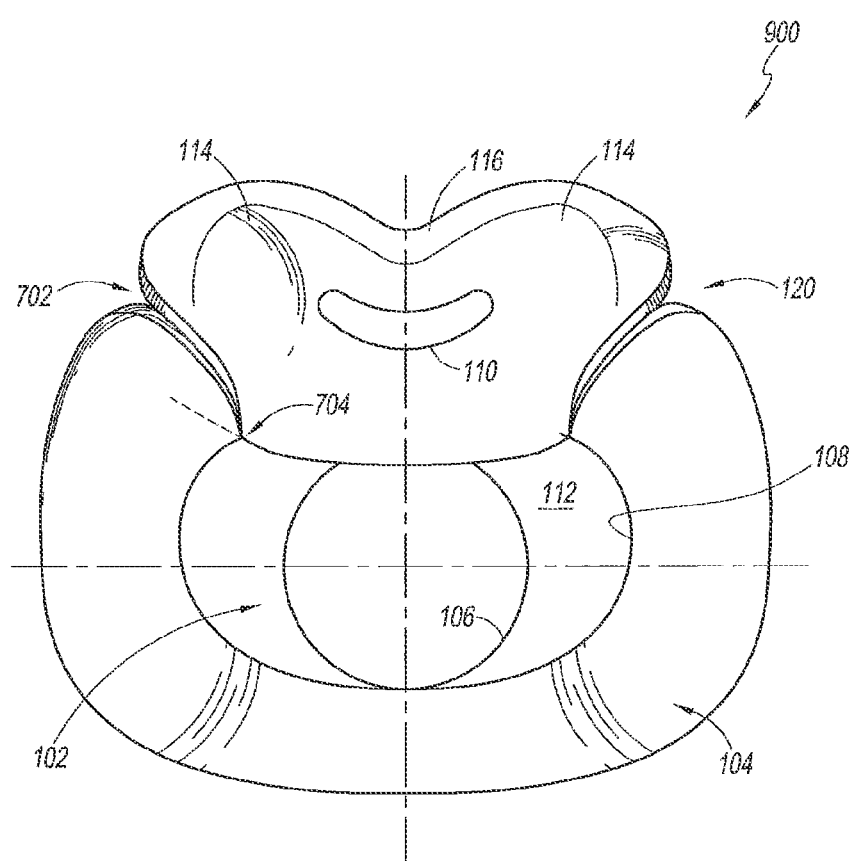
FIG. 22 is a rear view of another mask assembly having certain features, aspects and advantages of a preferred embodiment.

FIG. 22 illustrates a mask 900 that is substantially similar to the mask 800. However, in the mask 900, the pivot points 704 of the fold defining the bellows feature 120 are located at or very near the terminal ends of the bellows feature 120, which can be located on or near the at least one oral opening 108. The end portions of the bellows feature 120 can gradually taper to the pivot points 704.

Figure 23:
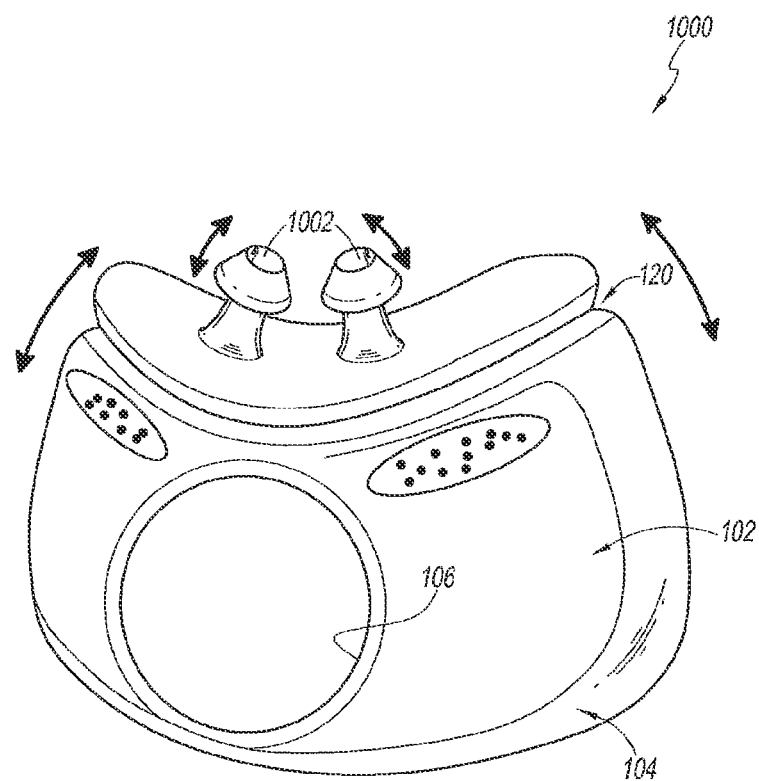
FIG. 23 is a front perspective view of another mask assembly having certain features, aspects and advantages of a preferred embodiment.

FIG. 23 illustrates a mask 1000 that is substantially similar to the masks 100, 200, 300, 400, 500, 600, 700, 800 and 900. Accordingly, the same reference numbers are used to indicate the same, similar or corresponding components or features. In addition, the mask 1000 is described in the context of differences relative to the masks 100, 200, 300, 400, 500, 600, 700, 800 and 900. Therefore, components or features that are not explicitly described with respect to the mask 700 can be assumed to be the same as or substantially similar to the corresponding components or features of the other masks described herein, or can be of another suitable arrangement. The mask 1000 includes a pair of nasal elements 1002 that extend from a body portion of the mask seal 104 and are configured to engage the nares of a user. In the illustrated arrangement, the nasal elements are nasal pillows, which can seal with the nares of the user. The mask 1000 integrates nasal engagement elements 1002 (e.g., nasal pillows) with a feature (e.g., bellows feature 120) that at least partially decouples movement of the nasal portion and the oral portions of the mask 1000. Any suitable decoupling arrangements can be used, such as any of the bellows features 120 described herein. Furthermore, in some configurations, the nasal elements 1002 can be used in combination with paddles 114 that contact the sides of the user's nose.

Figure 24:
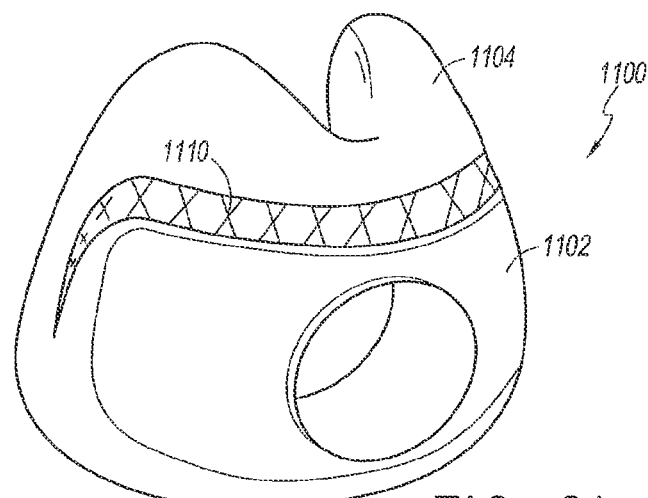
FIG. 24 is a front perspective view of another mask assembly having certain features, aspects and advantages of a preferred embodiment.
Figure 25:
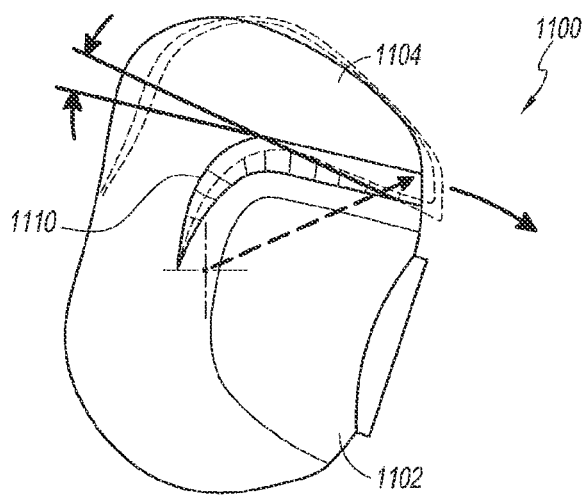
FIG. 25 is a side view of the mask assembly of FIG. 24.
Figure 26:
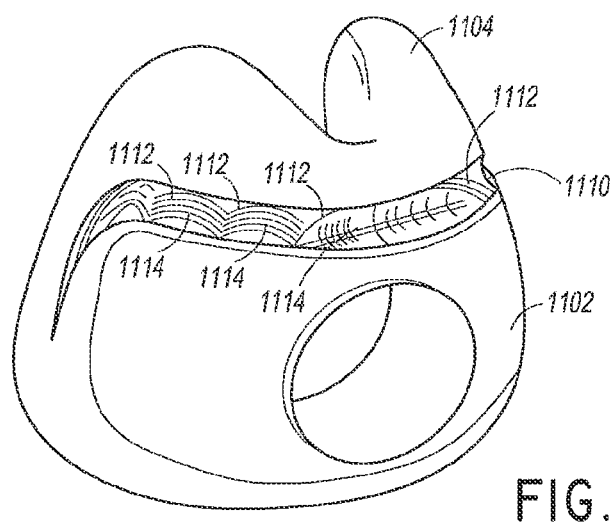
FIG. 26 is a front perspective view of another mask assembly having certain features, aspects and advantages of a preferred embodiment.

FIGS. 24-26 illustrate additional mask assemblies 1100, which can be similar to the mask assemblies 100, 200, 300, 400, 500, 600, 700, 800, 900 or 1000 described above. Accordingly, the mask assemblies 1100 are described in the context of the differences relative to the above-described mask assemblies. Any features or structures not discussed can be assumed to be the same as or similar to the corresponding features or structures of the above-described mask assemblies, or can be of another suitable arrangement. The mask assemblies 1100 can include a mask shell 1102 and a mask seal 1104. The mask seal 1104 can include one or more features tending to decouple movement of the nasal and oral portions of the mask seal 1104. Such features can be configured for preferential deformation relative to other portions of the mask seal 1104. Such decoupling can provide comfort, accommodate a larger range of nose profiles or tolerance to movement. Such decoupling can also help manage deformation of the mask seal 1104 when fitted on a user's face and when pressurized by gas within the mask seal 1104 to limit, inhibit or prevent undesirable creasing of portions of the mask seal 1104, which could result in or increase the chances of leaking.

For example, with reference to FIGS. 24 and 25, the mask seal 1104 can comprise a crease 1110 that extends along the mask seal 1104 generally between an upper or nasal portion of the mask seal 1104 and a lower or oral portion of the mask seal 1104. In the illustrated arrangement, the crease 1110 extends across a front wall of the mask seal 1104 above the upper edge of the mask shell 1102. The crease 1110 can extend an entire length of the mask shell 1102 and/or an entirety or a substantial entirety of a width of the mask seal 1104. In the illustrated arrangement, ends of the crease 1110 curve downwardly along portions of the sides of the mask shell 1102. The crease 1110 can generally follow the shape of the upper edge and, in some cases, the sides of the mask shell 1102.

The crease 1110 can comprise a suitable arrangement to facilitate deformation of the crease 1110 preferably instead of surrounding portions of the mask seal 1104. For example, the crease 1110 can comprise a region of smaller thickness relative to portions of the mask seal 1104 surrounding the crease 1110. The crease 1110 can have a constant thickness throughout a height and/or length direction of the crease 1110 or can vary in thickness.

FIG. 25 illustrates movement of the nasal portion of the mask seal 1104 relative to an oral portion of the mask seal 1104 facilitated by the crease 1110. In some configurations, an upper edge of the crease 1110 can move downwardly to a deformed position in response to pressure applied to the nasal portion, such as from the nose of a user, to define an angle relative to an original or relaxed position of the upper edge of the crease 1110. In some configurations, the nasal portion of the mask seal 1104 can move forward and down in response to applied pressure. A portion of the nasal portion above the crease 1110 can rotate about a natural pivot axis, which can be a virtual axis passing generally rearward of the mask shell 1102 and/or near ends of the crease 1110.

FIG. 26 illustrates a mask assembly 1100 having an alternative crease 1110, which comprises corrugated shape. For example, the crease 1110 can include peaks or ridges 1112, which can extend in a height direction of the crease 1110 or between opposing (e.g., upper and lower) edges of the crease 1110. The crease 1110 defines valleys 1114 between adjacent ridges 1112. The ridges 1112 can be oriented perpendicular to the edges of the crease 1110, or can be angled relative to the edges of the crease 1110, as illustrated in FIG. 26. The ridges 1112 can be oriented with the lower ends positioned laterally outward of the upper ends, or can have any other desirable orientation. The ridges 1112 can be straight or curved, as shown. The ridges 1112 can have other suitable shapes, as well. The presence of the ridges 1112 and valleys 1114 can provide folds of material, which can unfold to allow translational movement of the nasal portion of the mask seal 1104 relative to an oral portion of the mask seal 1104 without tensioning the material or with less tensioning than if the folds or corrugations were not present. In some configurations, the folds or corrugations can influence a direction of deformation of the crease 1110, such as by providing for variable deformation at different locations along the length of the crease 1110.

Figure 27:
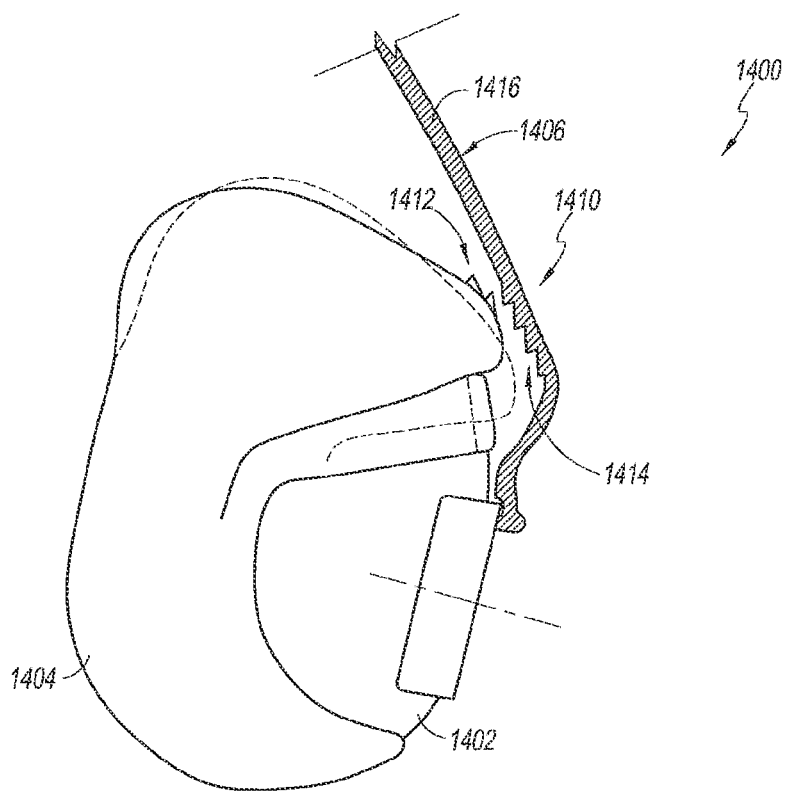
FIG. 27 a side, partial sectioned view of an interface assembly having certain features, aspects and advantages of a preferred embodiment.
Figure 28:
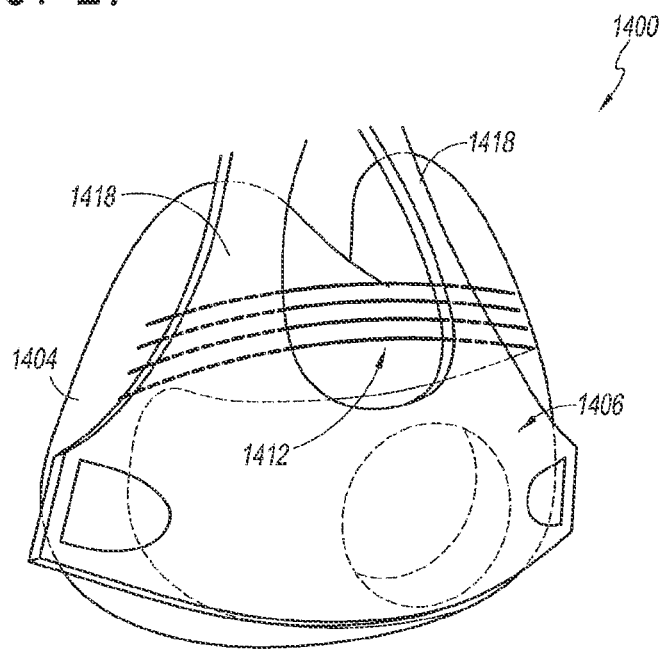
FIG. 28 is a front perspective view of the interface assembly of FIG. 27.

FIGS. 27 and 28 illustrate an interface assembly having a mask assembly 1400, which comprises a mask shell 1402 and a mask seal 1404. The interface assembly preferably also comprises a frame 1406. The mask assembly 1400 and frame 1406 can be the same as or similar to other mask assemblies and frames disclosed herein, for example. In some configurations, the mask seal 1404 includes one or more features that decouple movement of the nasal portion and the oral portion. Such features can be a crease, fold, bellows feature or other suitable structure, such as any of those described herein. Alternatively, the decoupling feature can be a rolling hinge or bellows arrangement similar to those disclosed in Applicant's PCI Publication No. WO2014/062070. In some configurations, no decoupling arrangement is present; however, preferably the mask seal 1404 is configured to permit some level of deformation of the nasal portion of the mask seal 1404.

The mask assembly 1400 and frame 1406 can include an arrangement that limits movement of the nasal portion of the mask seal 1404 in at least one direction and under at least some circumstances. Such an arrangement is referred to herein as a movement limiting arrangement 1410. The movement limiting arrangement 1410 can be configured to limit, inhibit or prevent upward movement of the nasal portion of the mask seal 1404, at least under certain circumstances. For example, in some configurations, the movement limiting arrangement 1410 limits upward movement of the nasal portion of the mask seal 1404 when the nasal portion is enlarged, such as a result of gas pressure within the mask seal 1404. In particular, the movement limiting arrangement 1410 can permit downward movement of the nasal portion of the mask seal 1404, such as a result of the user's nose pressing down on the nasal portion when the mask seal 1404 is fitted to the user's face. The movement limiting arrangement 1410 can remain disengaged or otherwise not substantially interfere with movement of the nasal portion of the mask seal 1404 when the nasal portion is not enlarged, such as when gas pressure within the mask seal 1404 is lower than a threshold pressure. Once the gas pressure within the mask seal 1404 rises above a threshold pressure, the movement limiting arrangement 1410 can engage to limit, inhibit or prevent upward movement of the nasal portion of the mask seal 1404. Such an arrangement can reduce the pressure that the nasal portion applies to the user's nose under high gas pressures within the mask seal 1401, such as pressures above the threshold pressure. The threshold pressure can be selected to provide desirable performance characteristics. For example, the threshold pressure could be set at or below a lower end of the treatment or therapy (e.g., CPAP) pressure such that the movement limiting arrangement 1410 is active at any therapy pressure. Alternatively, the threshold pressure could be set within the therapy or treatment pressure range such that the movement limiting arrangement 1410 is only active at relatively higher pressures within the range.

The movement limiting arrangement 1410 can be of any suitable structure to limit movement of the nasal portion of the mask seal 1404 relative to the oral portion. In the illustrated arrangement, the movement limiting arrangement 1410 comprises a ratchet assembly having a first ratchet portion 1412 attached to, formed by or otherwise carried by the nasal portion of the mask seal 1404 and a second ratchet portion 1414 attached to, formed by or otherwise carried by the frame 1406. The first ratchet portion 1412 and the second ratchet portion 1414 can each comprise ratchet teeth configured to permit downward movement of the first ratchet portion 1412 and the second ratchet portion 1414. At gas pressures below the threshold pressure, the first ratchet portion 1412 can be disengaged from the second ratchet portion 1414 such that upward movement of the first ratchet portion 1412 is permitted relative to the second ratchet portion 1414. At gas pressures above the threshold pressure, the first ratchet portion 1412 can engage the second ratchet portion 1414 to limit, inhibit or prevent upward movement of the first ratchet portion 1412 relative to the second ratchet portion 1414. As described above, the first ratchet portion 1412 and the second ratchet portion 1414 can be positioned for engagement as a result of enlargement or expansion of the nasal portion in response to gas pressure above the threshold pressure within the mask seal 1404. In some configurations, other methods of providing for selective engagement of the first ratchet portion 1412 and the second ratchet portion 1414 can be utilized.

The illustrated frame 1406 of FIG. 27 includes a T-piece portion 1416 that extends upwardly from the mask assembly 1400 and can rest against the user's forehead. The movement limiting arrangement 1410 can be provided on the T-piece portion 1416. In some configurations, the movement limiting arrangement 1410 can be provided on other portions of the frame 1406, such as when a T-piece portion 1416 is not provided, which portion can be provided specifically to accommodate the movement limiting arrangement 1410.

FIG. 28 illustrates a frame 1406 having a pair of vertical frame portions 1418, which can be laterally spaced from one another. In some configurations, a movement limiting arrangement 1410 can be provided on each of the vertical frame portions 1418 such that each side of the mask seal 1404 can engage one of the vertical frame portions 1418. As illustrated, the mask seal 1404 can include a single first ratchet portion 1412 that extends laterally across the mask seal 1404 and can engage each of the vertical frame portions 1418. In other configurations, separate first ratchet portions 1412 can be provided for each of the vertical frame portions 1418. In some configurations, the vertical frame portions 1418 can be sized, shaped and/or located to function as blocking members or covers for the upper portion, nasal portion or paddles of the mask seal 1404 and can limit forward and/or outward relative movement of the upper portion, nasal portion or paddles when the mask assembly 1400 is assembled to the frame 1406. In some such configurations, the frame 1406 is a common frame size connectable to mask assemblies of various or multiple sizes.

Figure 29:
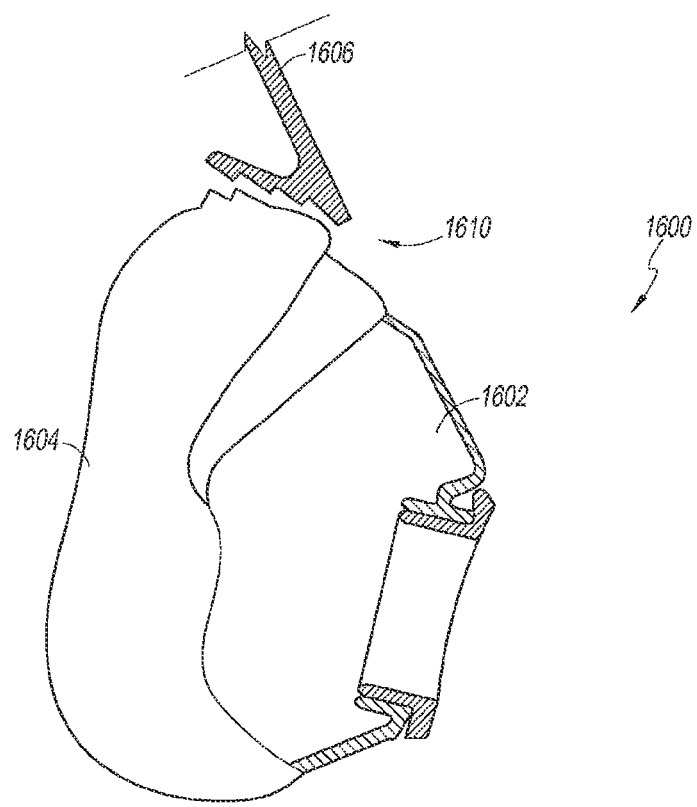
FIG. 29 is a side, partial sectioned view of an interface assembly having certain features, aspects and advantages of a preferred embodiment.
Figure 30:
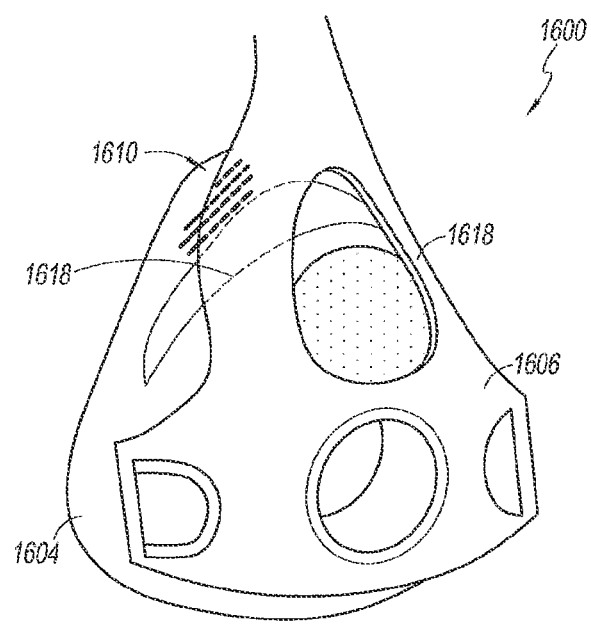
FIG. 30 is a front perspective view of the interface assembly of FIG. 29.

FIGS. 29 and 30 illustrate a movement limiting arrangement 1610 incorporated on a full face mask assembly 1600, which includes a mask shell 1602 and a mask seal 1604 that extends over the bridge of the nose of the user. The mask assembly 1600 can incorporate one or more features that decouple movement of the nasal portion and the oral portion. Such feature can be a crease, a rolling hinge, bellows arrangement or other suitable arrangement. The movement limiting arrangement 1610 can be the same as or similar to the above-described movement limiting arrangement 1410, or can be of any other suitable arrangement. The movement limiting arrangement 1610 can be centrally-located, as illustrated in FIG. 29, or can be located on lateral sides of the mask assembly 1600, as illustrated in FIG. 30. Similar to the arrangement of FIG. 28, the frame 1606 can include spaced-apart vertical portions 1618. In other arrangements, the frame 1606 can have a large lateral dimension, which can support the movement limiting arrangement 1610 on the sides of the mask seal 1604.

Figure 31:
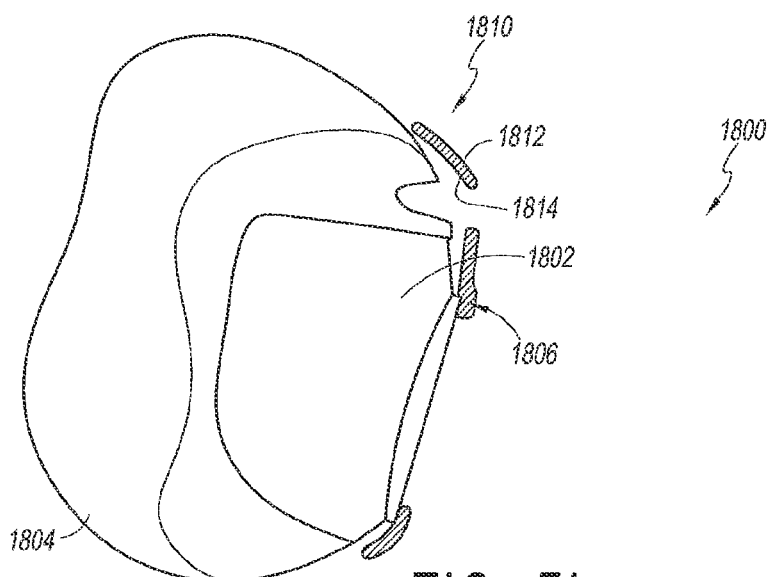
FIG. 31 is a side, partial sectioned view of an interface assembly having certain features, aspects and advantages of a preferred embodiment.

FIG. 31 illustrates a mask assembly 1800, which includes a mask shell 1802 and a mask seal 1804. The mask assembly 1800 can be the same as or similar to the other mask assemblies described herein, or can be of another suitable construction. The mask assembly 1800 can incorporate one or more features that decouple movement of the nasal portion and the oral portion. Such feature can be a crease, a rolling hinge, bellows arrangement or other suitable arrangement. The interface assembly includes a frame 1806, which incorporates an alternative movement limiting arrangement 1810 relative to those illustrated in FIGS. 27-30.

The movement limiting arrangement 1810 of FIG. 31 includes a cowling 1812 or other structure having an abutment surface 1814. The mask seal 1804 can contact the abutment surface 1814 to limit movement of a portion of the mask seal 1804. For example, the nasal portion of the mask seal 1804 can contact the abutment surface 1814 upon expansion such that the cowling 1812 limits further movement of the nasal portion of the mask seal 1804. The cowling 1812 cart limit further outward expansion of the nasal portion and/or can limit upward or backward movement of the nasal portion due to friction between the nasal portion and the abutment surface 1814, for example. The cowling 1812 can be supported by the frame 1806, can be integrated or unitary with the frame 1806 or can be otherwise supported in a desired position relative to the frame 1806. The cowling 1812 can be sized and shaped to interact with a desired portion of the mask seal 1804. For example, the cowling 1812 can have a portion that is centrally located relative to the mask seal 1804 and/or can have portions located on the sides of the mask seal 1804.

Figure 32:
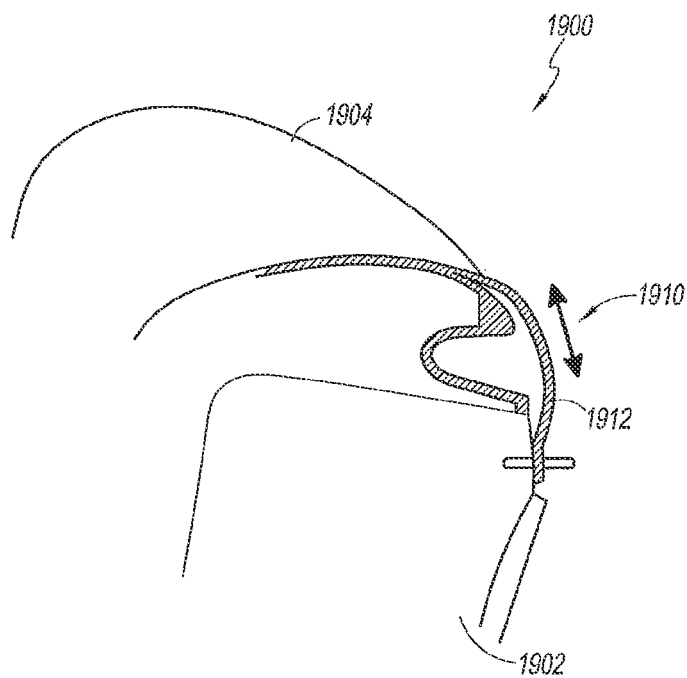
FIG. 32 is a side, partial sectioned view of an alternative interface assembly similar to that of FIG. 31.

FIG. 32 illustrates another movement limiting arrangement 1910 comprising a tether 1912 that is coupled to the nasal portion of a mask seal 1904 to limit movement of the nasal portion relative to an oral portion of the mask seal 1904. Similar to masks described above, the mask assembly 1900 of FIG. 32 can incorporate one or more features that decouple movement of the nasal portion and the oral portion. Such feature can be a crease, a rolling hinge, bellows arrangement or other suitable arrangement. The tether 1912 can have a first end portion coupled to the nasal portion of the mask seal 1904 and a second end portion coupled to the mask shell 1902, for example. The tether 1912 can have a length selected to provide a desired restriction on movement of the nasal portion of the mask seal 1904. The tether 1912 can be otherwise configured to limit movement of the nasal portion, such as a rigid tether having one end that is capable of limited movement. For example, an end of a rigid tether could be movable within a slot in the mask shell 1902. In the illustrated arrangement, the tether 1912 is unitarily formed with the mask seal 1904. However, in other arrangements, the tether 1912 could be otherwise coupled to the mask seal 1904.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. An interface for use in providing positive pressure respiratory therapy, the interface comprising a mask assembly comprising:
    a mask seal joined to a mask shell, the mask shell comprising a mask wall, the mask seal comprising a nasal portion and an oral portion, the mask seal comprising one or more features that decouple movement of the nasal portion of the mask seal relative to the oral portion of the mask seal, and
    a tether comprising a first end portion coupled to the nasal portion of the mask seal, the tether also comprising a second end portion coupled to the mask shell, the tether limiting movement of the nasal portion of the mask seal above a threshold distance away from the oral portion of the mask seal, and the tether being unitarily formed with the mask seal, wherein the tether only limits movement of the nasal portion of the mask seal away from the oral portion of the mask seal.

2. The interface of claim 1, wherein the nasal portion of the mask seal comprises a nasal region having an upper support surface, the nasal portion of the mask seal comprising a first paddle and a second paddle with the upper support surface of the nasal region being positioned between the first paddle and the second paddle such that an upwardly-open valley is defined by the first paddle, the upper support surface, and the second paddle, and at least a portion of at least one nasal opening extending through the upper support surface within the upwardly-open valley.

3. The interface of claim 1, wherein the one or more features that decouple movement comprise an upper wall portion positioned directly above a lower wall portion, the upper wall portion and the lower wall portion being moveable toward and away from one another.

4. The interface of claim 3, wherein the upper wall portion and the lower wall portion are generally linear and define a V-shape in cross-section.

5. The interface of claim 3, wherein at least one of the upper wall portion and the lower wall portion have a curved shape in cross-section.

6. The interface of claim 1, wherein the one or more features that decouple movement comprise a first wall portion and a second wall portion, the first wall portion and the second wall portion being arranged at an angle relative to one another.

7. The interface of claim 6, wherein the first wall portion and the second wall portion cooperate to define an L-shape in cross-section.

8. The interface of claim 7 further comprising a curved wall portion between the second wall portion and a portion of the mask wall adjacent the one or more features that decouple movement of the nasal portion of the mask seal relative to the oral portion of the mask seal.

9. The interface of claim 7, wherein the first wall portion is shaped similarly to a front wall of the nasal portion of the mask seal.

10. The interface of claim 1, wherein the one or more features that decouple movement of the nasal portion of the mask seal relative to the oral portion of the mask seal extend at least to a transition between a side surface of the mask assembly and a user-facing surface of the mask assembly.

11. The interface of claim 10, wherein the one or more features that decouple movement of the nasal portion of the mask seal relative to the oral portion of the mask seal define an invert point at or near the transition.

12. The interface of claim 11, wherein the one or more features that decouple movement of the nasal portion of the mask seal relative to the oral portion of the mask seal taper in height and or depth toward the invert point.

13. The interface of claim 11, wherein the one or more features that decouple movement of the nasal portion of the mask seal relative to the oral portion of the mask seal comprise a corrugated arrangement.

14. The interface of claim 11, wherein the one or more features that decouple movement comprise a crease or bellows.

15. The interface of claim 1, wherein the tether has a length comprising the threshold distance, the length selected to restrict movement of the nasal portion of the mask seal away from the oral portion of the mask seal.

16. The interface of claim 1, wherein the tether is rigid.

17. The interface of claim 1, wherein the mask shell comprises a central portion, a pair of wings sweeping rearwardly of the central portion, and an opening for a connector formed in the central portion.

18. The interface of claim 1, wherein the one or more features that decouple movement of the nasal portion of the mask seal relative to the oral portion of the mask seal also limit movement of the nasal portion of the mask seal toward the oral portion of the mask seal.

* * * * *